United States Patent [19]

Plattner et al.

[11] 4,001,263
[45] Jan. 4, 1977

[54] 5-ARYL-1,2,3,4-TETRAHYDRO-γ-CARBOLINES

[75] Inventors: Jacob J. Plattner, East Lyme; Charles A. Harbert; James R. Tretter, both of Waterford, all of Conn.

[73] Assignee: Pfizer Incorporated, New York, N.Y.

[22] Filed: Apr. 9, 1975

[21] Appl. No.: 566,354

Related U.S. Application Data

[63] Continuation-in-part of Ser. No. 456,640, April 1, 1974, abandoned.

[52] U.S. Cl. .................. 260/296 A; 260/240 R; 260/240 K; 260/294.9; 260/295 C; 424/263; 424/274
[51] Int. Cl.$^2$ .................................. C07D 471/04

[58] Field of Search ............... 260/296 A, 295 C

[56] References Cited
UNITED STATES PATENTS
3,654,289   4/1972   Paris et al. ............... 260/296 A FOREIGN PATENTS OR APPLICATIONS
721,171   12/1954   United Kingdom Primary Examiner—Henry R. Jiles
Assistant Examiner—R. W. Ramsuer
Attorney, Agent, or Firm—Connolly and Hutz

[57] ABSTRACT

2-Substituted-5-aryl-1,2,3,4-tetrahydro-γ-carbolines, their use as tranquilizing agents and the preparation thereof from 5-aryl-1,2,3,4-tetrahydro-γ-carbolines.

25 Claims, No Drawings

5-ARYL-1,2,3,4-TETRAHYDRO-γ-CARBOLINES

BACKGROUND OF THE INVENTION

Following the introduction of reserpine and chlorpromazine in psychotherapeutic medicine in the early 1950's, great effort has been expended in the search for other tranquilizing agents having improved biological profiles.

It has now been found certain indoles, and more particularly, a series of 2-substituted-5-aryl-1,2,3,4-tetrahydro-γ-carbolines, are extremely effective as tranquilizing agents.

γ-Carbolines are not new in the chemical and patent literature; antihistamine activity is claimed in British Pat. No. 721,171, and U.S. Pat. Nos. 2,786,059 and 3,409,628; antidepressant activity in U.S. Pat. Nos. 3,419,568, 3,687,960, 3,705,902 and 3,718,657; antitrypanosomal activity in U.S. Pat. No. 3,654,289 and German Pat. Nos. 2,117,286 and 2,115,738; depressant and analgesic activity in U.S. Pat. Nos. 3,466,293, 3,502,688 and 3,382,250; and tranquilizing activity in U.S. Pat. Nos. 3,687,961 and 3,755,584.

SUMMARY OF THE INVENTION

The tranquilizing agents of this invention are represented by the formula

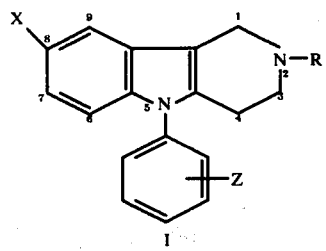

I and the pharmaceutically acceptable acid addition salts thereof, wherein X is fluoro, chloro, bromo or hydrogen; Z is hydrogen, fluoro, chloro or methoxy; and R is benzyl or substituted alkylene of the formula

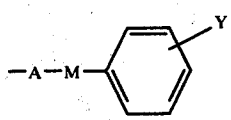

wherein A is alkylene of 1 to 5 carbon atoms, M is —CH=CH—, —CH$_2$—,

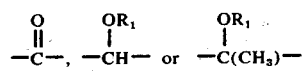

wherein R$_1$ is hydrogen or alkanoyl of 2 to 9 carbon atoms and Y is fluoro, chloro, methyl or hydrogen.

A preferred group of chemotherapeutic compounds of the instant invention are those of formula I wherein X and Z are as indicated and R is substituted alkylene of the formula

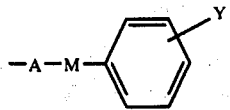

where A is alkylene of 1 to 5 carbon atoms, Y is as indicated and M is

A second preferred group of chemotherapeutic agents of formula I are those wherein X and Z are as previously indicated and R is substituted alkylene of the formula

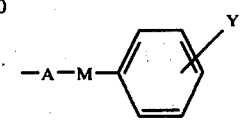

where A is alkylene of 1 to 5 carbon atoms, Y is as previously defined and M is

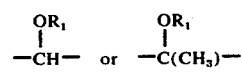

where R$_1$ is hydrogen.

A third preferred group of compounds of formula I are those wherein X and Z are as previously defined and R is substituted alkylene of the formula

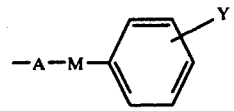

where A is alkylene of 1 to 5 carbon atoms, Y is as previously defined and M is

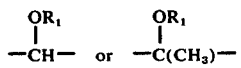

where R$_1$ is alkanoyl of 2 to 9 carbon atoms.

A second class of therapeutically active compounds of the present invention are those of formula II

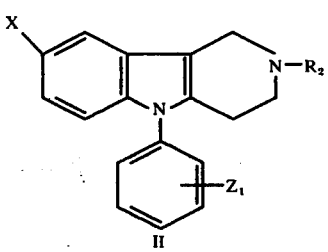

II and the pharmaceutically acceptable acid addition salts thereof, wherein

X is hydrogen, fluoro, chloro or bromo; $Z_1$ is fluoro, chloro or methoxy; and $R_2$ is alkyl of 1 to 6 carbon atoms.

A preferred group of compounds related to those of formula II are those wherein X is fluoro and $Z_1$ and $R_2$ are as previously defined.

A third class of compounds of the present invention which are useful as intermediates leading to the therapeutic compounds of formulae I and II are those of the formula

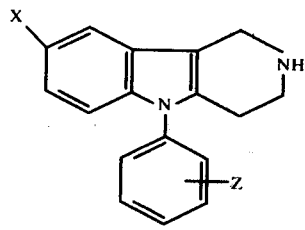

wherein X is hydrogen, fluoro, chloro or bromo and Z is hydrogen, fluoro, chloro or methoxy.

A preferred group of compounds within this class of intermediates are those wherein Z is as previously defined and X is fluoro.

Also considered within the purview of the present invention are congeners of the formula

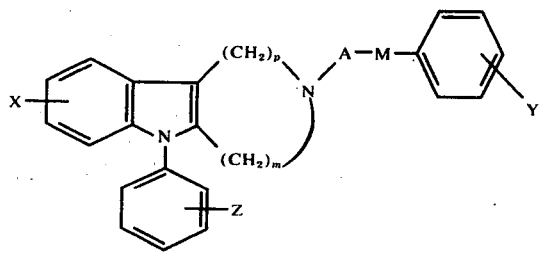

wherein X, Y, Z, M and A are as previously defined, and m is an integer of 2 and p is an integer of 1 or 2.

The compounds of the present invention demonstrated a marked, and unexpected superior tranquilizing effect over the closest compounds known, namely 5-phenyl-2-methyl-1,2,3,4-tetrahydro-γ-carboline in British Pat. No. 721,171 and 5-phenyl-2-benzyl-1,2,3,4-tetrahydro-γ-carboline as described by Spickett, *J. Med. Chem.*, 9, 436 (1966).

DETAILED DESCRIPTION OF THE INVENTION

In accordance with the process employed for synthesizing the compounds of the present invention the following scheme is illustrative:

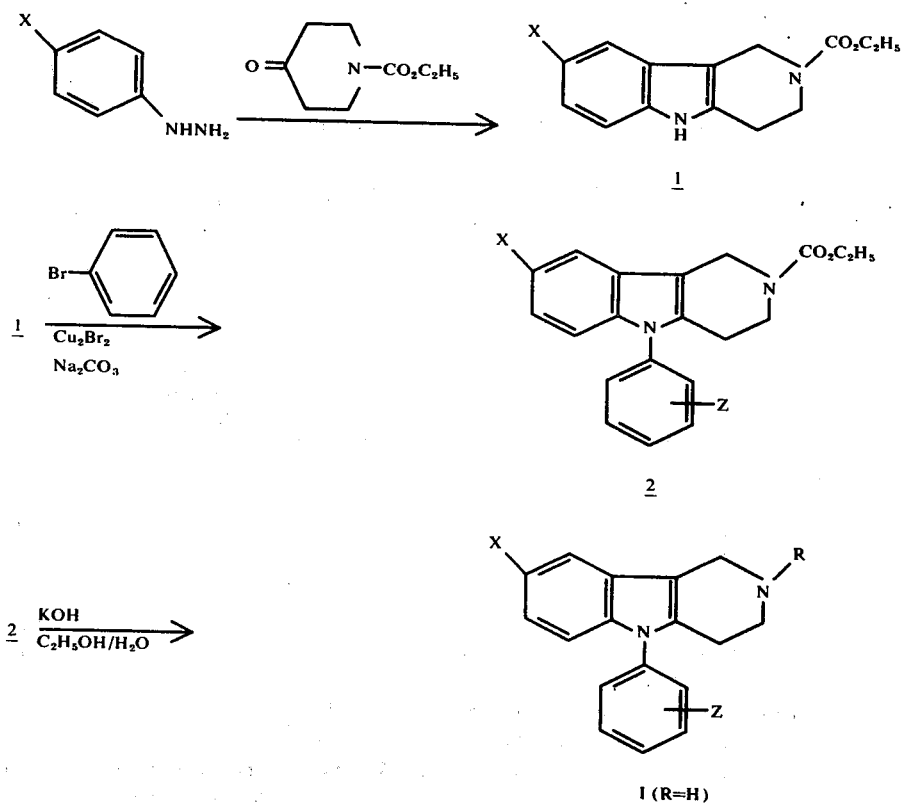

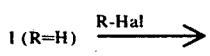 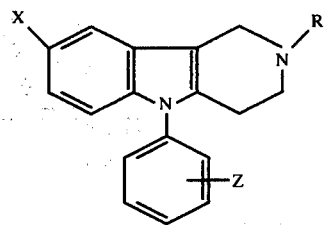

wherein X and Z are as previously defined, Hal is a halogen or sulfonate ester and R is hydrogen, benzyl or substituted alkylene of the formula

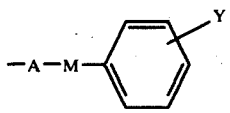

wherein A is alkylene having 1 to 5 carbon atoms, M is —CH₂— or

and Y is as previously defined.

In practice, the γ-carbolines of formula 1 are conveniently prepared from the commercially-available 1-carbethoxy-4-piperidone and the requisite phenylhydrazines by the classical Fischer indole synthesis which comprises heating approximately equimolar amounts of the appropriate phenylhydrazine hydrochloride with the piperidone in a reaction-inert solvent such as absolute ethanol.

Arylation of 1 is effected through the reaction of 1 with a suitably substituted halobenzene derivative, employing a 2–3 fold molar excess of the bromobenzene derivative for optimum yields of the product, 2. In addition, equimolar amounts, plus as much as a 100% excess, of cuprous bromide and sodium carbonate are employed in this reaction, said reaction being conducted in a reaction-inert solvent such as nitrobenzene, hexamethylphosphoramide or N-methyl-2-pyrrolidione at a temperature of 125°–225° C. with a preferred range of 175°–200° C.

Hydrolysis of compounds related to 2 is effected by heating an ethanol solution of the appropriate 2-carbethoxy-5-aryl-1,2,3,4-tetrahydrocarboline with at least two molar equivalents of potassium hydroxide.

This sequence of reactions is preferred for the preparation of the useful intermediates of the instant invention of formula I, where R represents hydrogen.

Compounds of formula I wherein X and Z are previously defined and R is alkyl, benzyl or substituted alkylene of the formula

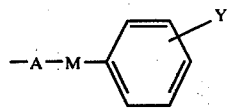

where A is alkylene, M is —CH₂— or

and Y is as previously defined are synthesized by alkylation of I wherein R is hydrogen.

Experimentally, the reaction is conducted with an equimolar amount, plus as much as a 10–20% excess, of the alkylating agent in a reaction-inert, aprotic, polar solvent, such as tetramethylensulfone, dimethylformamide, dimethysulfoxide, hexamethylphosphoramide or a dialkyl ketone, at elevated temperatures. To facilitate the completion of the reaction a catalytic amount of potassium iodide is added to the reaction mixture, forming in situ reactive amounts of the iodo alkylating agent. In addition, a five to six mole excess of sodium carbonate is added as a scavenger for the hydrogen halide produced as a by-product in said alkylation.

Several additional synthetic pathways can be employed in the preparation of compounds of formula II, wherein R₂ is alkyl. The first alternate route employs the use of the initial reaction of a phenylhydrazine derivative with a 1-alkly-4-piperidone followed by arylation of the 5-position; this reaction scheme is illustrated as follows:

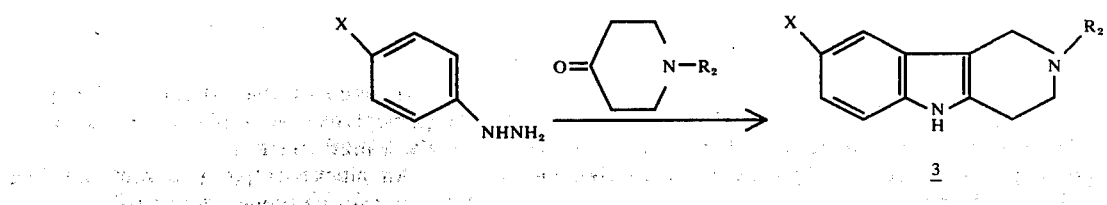

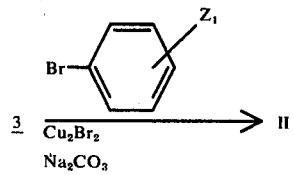

The conditions of the Fischer indole synthesis leading to 3 and the subsequent arylation reaction of 3 leading to II are similar to those previously described.

The second alternate synthetic scheme leading to 2-alkyl-5-aryl-1,2,3,4-tetrahydro-γ-carbolines employs acylation of formula I wherein R is hydrogen with an appropriate acid halide, anhydride or mixed anhydride, followed by a metal hydride reduction of the formed amide, according to the following illustrative route:

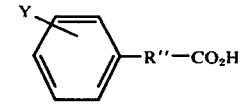

wherein Y is as previously defined and R'' is alkylene of from 1 to 5 carbon atoms.

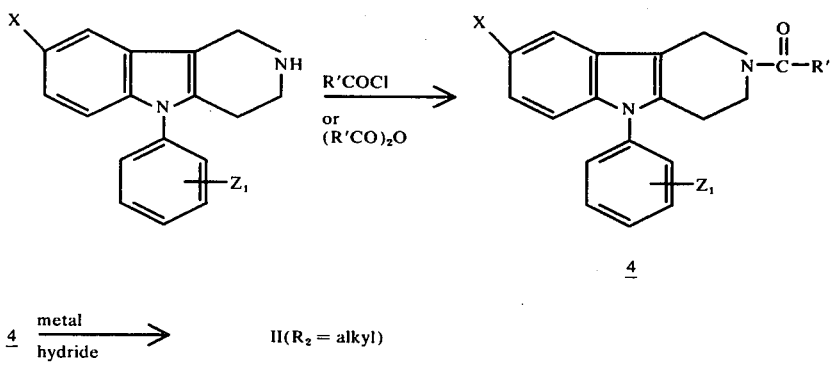

wherein X and $Z_1$ are as previously defined and R' is alkyl containing from 1 to 5 carbon atoms.

In practice, the acylation of compounds of formula I (R = H), shown above, is effected with an acid halide, anhydride or mixed anhydride employing equimolar amounts of the acylating agent plus as much as a 20% excess in a reaction-inert solvent such as a chlorinated hydrocarbon. An equimolar amount, plus as much as a two-fold excess, of a tertiary amine, such as triethyl amine, is added to facilitate the completion of the reaction, which can be conducted at ambient temperatures.

Reduction of compounds of formula 4 is most conveniently achieved employing a metal hydride such as lithium aluminum hydride or aluminum hydride in a action-inert solvent such as one of the dialkyl or cyclo-alkyl ethers.

Similarly, acylation can be carried out with the corresponding acid halide or anhydride of an arylalkanoic acid of the formula:

Reduction of the formed amides, similar to 4 is effected using lithium aluminum hydride or aluminum hydride and provides compounds wherein the 2-substituent is aralkyl of the formula

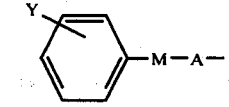

wherein Y, M and A are as defined.

A third synthetic pathway to compounds of formula I where R is methyl comprises a lithium aluminum hydride or aluminum hydride reduction of compounds of formula 2 as follows

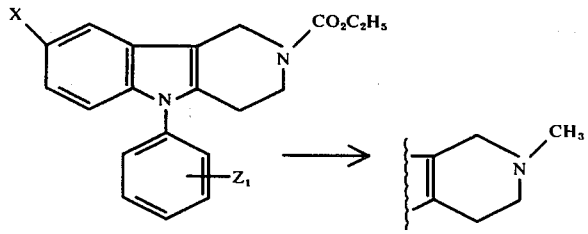

As one skilled in the art can readily appreciate, any carboalkoxy can be employed in this route leading to the 2-methyl congeners.

An alternative preparative route leading to compounds of formula I wherein R is

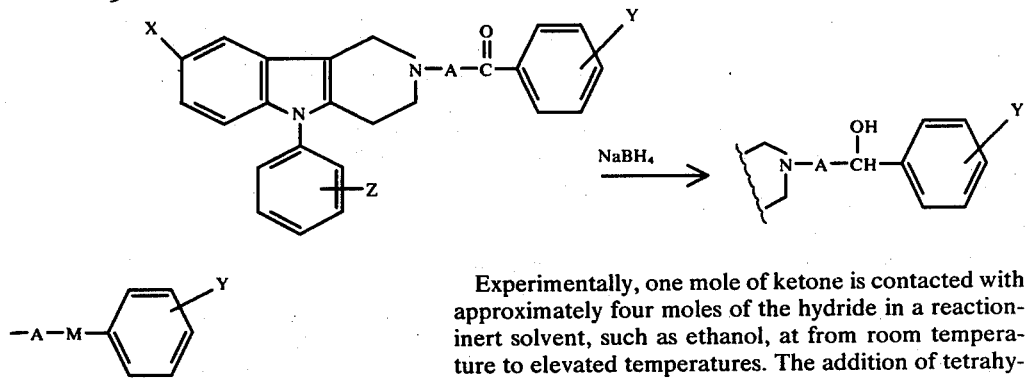

where A and X are as previously defined and M is

is shown in the following flow diagram:

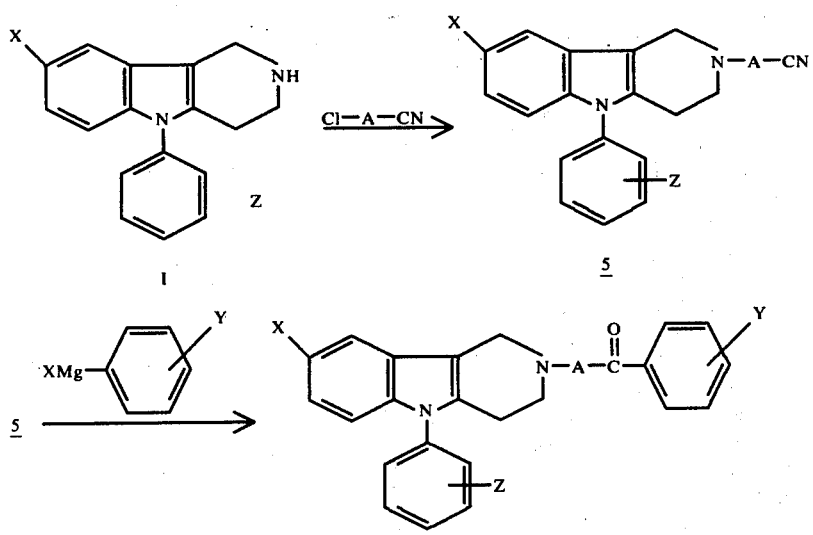

Alkylation of compounds of formula I (R = H) with an ω-haloalkyl nitrile is effected under the same alkylation conditions previously described.

Further reaction of the nitrile, 5, with the requisite Grignard reagent leads to the desired ketones. It is preferred that four moles of Grignard reagent per mole of nitrile be employed, although the desired product can be prepared with less of an excess. As with Grignard reactions, it is preferred that the reaction be conducted in a reaction-inert solvent such as diethyl ether.

Synthesis of compounds for formula I wherein R is

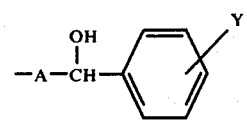

wherein A and Y are as previously defined are effected by reduction of the corresponding ketone employing sodium borohydride as illustrated in the following scheme:

Experimentally, one mole of ketone is contacted with approximately four moles of the hydride in a reaction-inert solvent, such as ethanol, at from room temperature to elevated temperatures. The addition of tetrahydrofuran facilitates the reaction by enhancing the solubility of the reactants.

The tertiary alcohols of the present invention are prepared by the reaction of the appropriate ketone with methyl magnesium iodide, illustrated as follows:

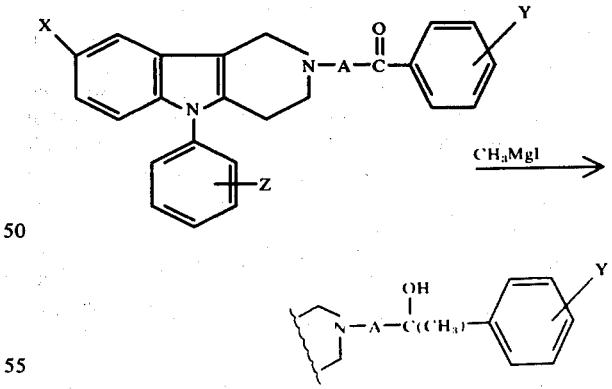

where X, Z, A and Y are as previously defined.

As in the previously described Grignard reaction, although the starting materials react in equimolar amounts, it is preferred that as much as a 100% excess of the methyl magnesium iodide be employed. In addition, it is also preferred that the reaction be conducted in a reaction-inert solvent such as diethyl ether at ambient temperatures.

The alcohols of the present invention are readily converted to esters by acylation with an acid halide, anhydride or mixed anhydride. These acylation reactions can be conducted in such solvents as chlorinated hydrocarbons employing a tertiary amine, such as pyridine or triethyl amine, to ensure completeness of the reaction.

The secondary alcohols of the instant invention, on treatment with 6N hydrochloric acid at elevated temperatures, are converted by dehydration to those congeners wherein M is —CH=CH—. It is frequently preferred that a cosolvent such as ethanol be employed in order to enhance the solubility of the carboline.

Regarding the equisite starting reagents leading to the synthesis of the compounds of the instant invention, they are either commercially available, their preparation is explicitly reported in the chemical literature or they can be prepared by methods known to those skilled in the art. For example, the phenylhydrazines are commercially available or are synthesized by reduction of the phenyldiazonium salt as reviewed by Wagner and Zook in "Synthetic Orgnaic Chemistry, " John Wiley & Sons, New Yor, N. Y., 1956, Chapter 26; the 1-substituted 4-piperidones are commercial reagents or prepared by the method of McElvain and Rorig, *J. Am. Chem. Soc.*, 70, 1826 (1948); and the ω-haloalkyl aryl ketones are synthesized by the method as taught in U.S. Pat. No. 2,997,472 (C.A. 56, 11603 [1962]).

As has been previously mentioned, the compounds of the present invention can form acid addition salts. Said basic compounds are converted to their acid addition salts by interaction of the base with an acid either in an aqueous or nonaqueous medium. In a similar manner, treatment of the acid addition salts with an equivalent amount of an aqueous base solution, e.g., alkali metal hydroxides, alkali metal carbonates and alkali metal bicarbonates or with an equivalent amount of a metal cation which forms an insoluble precipitate with the acid anion, results in the regeneration of the free base form. The bases thus regenerated may be reconverted to the same or a different acid addition salt.

In the utilization of the chemotherapeutic activity of those compounds of the present invention, it is preferred, of course, to use pharmaceutically acceptable salts. Although water-insolubility, high toxicity, or lack of crystalline nature may make some particular salt species unsuitable or less desirable for use as such in a given pharmaceutical application, the water insoluble or toxic salts can be converted to the corresponding pharmaceutically acceptable bases by decomposition of the salt as described above, or alternately, they can be converted to any desired pharmaceutically acceptable acid addition salt.

Examples of acids which provide pharmaceutically acceptable anions hydrochloric, hydrobromic, hydroiodic, nitric, sulfuric, or sulfurous, phosphoric, acetic, lactic, citric, tartaric, succinic, maleic and gluconic acids.

As previously indicated, the γ-carbolines of the present invention are, with the exception of those compounds of formula I wherein R is hydrogen, said compounds being useful as intermediates, are readily adapted to therapeutic use as tranquilizing agents in mammals. Outstanding for their effectiveness in these regards are the following agents: 8-fluoro-5-(p-fluorophenyl)-2-[3-(p-fluorobenzoyl)propyl]-1,2,3,4-tetrahydro-γ-carboline, 8-chloro-5-(p-fluorophenyl)-2-[3-(p-fluorobenzoyl)propyl]-1,2,3,4-tetrahydro-γ-carboline, 8-fluoro-5-(p-chlorophenyl)-2-[3-(p-fluorobenzoyl)propyl]-1,2,3,4-tetrahydro-γ-carboline, 8-fluoro-5-phenyl-2-[3-(p-fluorobenzoyl) propyl]1,2,3,4-tetrahydro-γ-carboline, 8fluoro-5-(p-fluorophenyl)-2-[4-(p-fluorophenyl)-4-hydroxybutyl]-1,2,3,4-γ-carboline, 8-fluoro-5-(p-fluorophenyl)-2-(4-phenyl-4-hydroxybutyl)-1,2,3,4-tetrahydroγ-carboline, 8-fluoro-5-(p-fluorophenyl)-2-[4-(p-chlorophenyl)-4-hydroxybutyl]-1,2,3,4-tetrahydro-γ-carboline, 8-fluoro-5-(p-fluorophenyl)-2-[4-(p-tolyl)-4-hydroxybutyl]-1,2,3,4-tetrahydro-γ-carboline, 8-fluoro-5-(p-fluorophenyl)-2-[3-(p-fluorophenyl)-3-hydroxypropyl]-1,2,3,4-γ-carboline, 8-fluoro-5-(p-fluorophenyl)-[5-(p-fluorophenyl)-5-hydroxypenty]-1,2,3,4-tetrahydro-γ-carboline, 8-fluoro-5-(m-fluorophenyl)-2-[4-(p-fluorophenyl)-4-hydroxybutyl]-1,2,3,4-tetrahydro-γ-carboline, 8-fluoro-5-(o-fluorophenyl)-2-[4-(p-fluorophenyl)-4-hydroxybutyl]-1,2,3,4-tetrahydro-γ-carboline, 8-5-(p-fluorophenyl)-2-[4-(p-fluorophenyl)-4-hydroxybutyl]-1,2,3,4-tetrahydro-γ-carboline, 8-bromo-5-(p-fluorophenyl)-2-[4(p-fluorophenyl)-4-hydroxybutyl]-1,2,3,4-tetrahydro-γ-carboline, 8-fluoro-5-(p-fluorophenyl)-2-[4-(m-fluorophenyl)-4-hydroxybutyl]-1,2,3,4-tetrahydro-γ-carboline, 8-fluoro-5-(p-anisyl)-2-[4-(p-fluorophenyl)-4-hydroxybutyl]-1,2,3,4-tetrahydro-γ-carboline, 8-fluoro-5-(p-anisyl)-2-[4-(p-toul)-4-hydroxybutyl]-1,2,3,4-tetrahydro-γ-carboline, 8-fluoro-5-(p-anisyl)-2-[4-(p-chlorophenyl)-4-hydroxybutyl]1,2,3,4-tetrahydro-γ-carboline, 8-chloro-5-phenyl-2-[4-(p-fluorophenyl)-4-hydroxybutyl]-1,2,3,4-tetrahydro-γ-carboline, 8-fluoro-5-phenyl-2-[4-(p-tolyl)-4-hydroxybutyl]-1,2,3,4-tetrahydro-γ-carboline, 8-chloro-5-phenyl-2-[4-(p-tolyl)-4-hydroxybutyl]-1,2,3,4-tetrahydro-γ-carboline, 8-5-(p-chlorophenyl)-2-[4-(p-fluorophenyl)-4-hydroxybutyl]-1,2,3,4-tetrahydro-γ-carboline, 8-fluoro-5-(p-chlorophenyl)-2-[4-(p-chlorophenyl)-4-hydroxybutyl]-1,2,3,4-tetrahydro-γ-carboline, 8-fluoro-5-(p-chlorophenyl)-2-(4-phenyl-4-hydroxybutyl)-1,2,3,4-tetrahydro-γ-carboline, 8-fluoro-5-(p-fluorophenyl)-2-[4-(p-fluorophenyl)-4-hydroxypentyl]-1,2,3,4-tetrahydro-γ-carboline, 8-fluoro-5-(p-fluorophenyl)-2-[4-(p-fluorophenyl)-4-hydroxypentyl]-1,2,3,4-tetrahydro-γ-carboline, 8-fluoro-5-phenyl-2-[4-(p-fluorophenyl)-4-hydroxypentyl]-1,2,3,4-tetrahydro-γ-carboline, 8-fluoro-5-(p-fluorophenyl)-2-[4-(p-fluorophenyl)-4-acetoxybutyl]-1,2,3,4-tetrahydro-γ-carboline, 8-fluoro-5-(p-fluorophenyl-2-[4-(p-fluorophenyl-4-valeryloxybutyl]-1,2,3,4-tetrahydro-γ-carboline, 8-fluoro-5-(p-fluoropheny)-2-[4-(p-fluorophenyl)-4-n-heptanoyloxybutyl]-1,2,3,4-tetrahydro-γ-carboline, 8-5-(p-fluorophenyl)-2-[4-(p-fluorophenyl)-3-butenyl]-1,2,3,4-tetrahydro-γ-carboline, 8-5-(p-fluorophenyl)-2-benzyl-1,2,3,4-tetrahydro-γ-carboline, 8-fluoro-5-(p-fluorophenyl)-2-methyl-1,2,3,4-tetrahydro-γ-carboline, 8-fluoro-5-(p-fluorophenyl)-2-ethyl-1,2,3,4tetrahydro-γ-carboline, 8-fluoro-5-(p-fluorophenyl)-2-n-propyl-1,2,3,4-tetrahydro-γ-carboline and 8-fluoro-5-(p-fluorophenyl)-2-(3,3-dimethyl-n-buty)-1,2,3,4-tetrahydro-γ-carboline.

The preferred intermediates leading to the tranquilizing products of the present invention are 8-fluoro-5-(p-fluorophenyl)-1,2,3,4-tetrahydro-γ-carboline, [-fluoro-5-(p-anisyl)-1,2,3,4-tetrahydro-γ-carboline, 8-fluoro-5-(p-chlorophenyl)-1,2,3,4-tetrahydro-γ-carboline and 8-fluoro-5-phenyl-1,2,3,4-tetrahydro-γ-carboline.

The tranquilizing agents of the present invention are characterized by relief of such schizophrenic manifestations in humans as hallucinations, hostility, suspiciousness, emotional or social withdrawal, anxiety, agitation and tension. Standard procedures of detecting and comparing tranquilizing activity of compounds in this series and for which there is an excellent correlation with human efficacy is the antagonism of amphetamine-induced symptoms in rats test, as taught by A. Weissman, et al., *J. Pharmacol. Exp. Ther.*, 151, 339 (1966) and by Quinton, et al.,*Nature*, 200, 178 (1963).

The γ-carbolines and the pharmaceutically acceptable salts thereof, which are useful as tranquilizers, can be administered either as individual therapeutic agents or as mixtures of therapeutic agents. They may be administered alone, but are generally administered with a pharmaceutical carrier selected on the basis of the chosen route of administration and standard pharmaceutical practice. For example, they can be administered orally in the form of tablets or capsules containing such excipients as starch, milk sugar, or certain types of clay, etc. They can be administered in the form of elixirs or oral suspensions with the active ingredients combined with emulsifying and/or suspending agents. They may be injected parenterally, and for this use they, or appropriate derivatives, may be prepared in the form of sterile aqueous solutions. Such aqueous solutions should be suitably buffered, if necessary, and should contain other solutes such as saline or glucose to render them isotonic.

Although the use of the present invention is directed toward the treatment of mammals in general, the preferred subject is humans. In determining an efficacious dose for human therapy, results of animal testing are frequently extrapolated and a correlation is assumed between animal test behavior and proposed human dosage. When a commercially employed standard is available, the dose level of the clinical candidate in humans is frequently determined by comparison of its performance with the standard in an animal test. For example, if a standard tranquilizing agent is administered effectively to humans at the rate of 100 to 400 mg. daily, it is assumed, then, that if compounds of the present invention have activity comparable to this standard in the test assay, that similar doses will provide comparable responses in humans.

Obviously, the physician will ultimately determine the dosage which will be most suitable for a particular individual, and it will vary with age, weight and response of the particular patient, as well as with the nature and extent of the symptoms and the pharmacodynamic characteristics of the particular agent to be administered. Generally, small doses will be administered initially, with a gradual increase in the dosage until the optimum level is determined. It will often be found that when the composition is administered orally, larger quantities of the active ingredient will be required to produce the same level as produced by a smaller quantity administered parenterally.

Having full regard for the foregoing factors, it is considered that a daily dosage of the compounds of the instant invention in humans of approximately 1 to 50 mg., with a preferred range of 1 to 25 mg., will tranquilize effectively. In those individuals in which the compounds of the present invention have a prolonged effect, the dose can be 5 to 125 mg. a week, administered in one or two divided doses. These values are illustrative, and there may, of course, be individual cases where higher or lower dose ranges are merited.

The following examples are provided solely for the purpose of illustration and are not to be construed as limitations of this invention, many variations of which are possible without departing from the spirit or scope thereof.

EXAMPLE 1

8-Fluoro-5-(p-fluorophenyl)-1,2,3,4-tetrahydro-γ-carboline

A. 8-fluoro-2-carbethoxy-1,2,3,4-tetrahydro-γ-carboline

A mixture of 15.9 g. (0.093 mole) of N-carbethoxy-4-piperidone and 15.1 g. (0.093 mole) of p-fluorophenylhydrazine hydrochloride in 150 ml. of ethanol is heated to reflux for 2 hrs. The reddish reaction mixture is cooled and filtered, and the collected solids washed with a small amount of cold 95% ethanol, 21.3 g. (88% yield), m.p. 169°–170° C. The analytical sample is recrystallized from ethanol-water, m.p. 169°–170° C.

Anal. Calc'd for $C_{14}H_{15}O_2N_2F$: C, 64.1; H, 5.8; N, 10.7. Found: C, 63.8; H, 5.8; N, 10.6.

B. 8-fluoro-5-(p-fluorophenyl)-2-carbethoxy-1,2,3,4-tetrahydro-γ-carboline

To 30 ml. of N-methyl-2-pyrrolidione is added 3.45 g. (0.013 mole) of 8-fluoro-2-carbethoxy-1,2,3,4-tetrahydro-γ-carboline, 7.8 g. (0.045 mole) of p-fluorobromobenzene, 4.14 g. (0.014 mole) of cuprous bromide and 1.5 g. (0.014 mole) of sodium carbonate, and the resulting mixture heated in an oil bath at 200° I C. for 6 hrs. The mixture is allowed to cool to room temperature overnight, and is then decanted into 300 ml. of water containing 60 ml. of ethylene diamine. Benzene (200 ml.) is added and the two-phase system is filtered through a super-cel pad. The filtrate is subsequently extracted several times with a total of 700 ml. of benzene. The extracts are combined, washed successively with water and a saturated brine solution and dried over anhydrous sulfate. Removal of the solvent provides the crude product as a dark, residual oil.

The crude product in benzene is chromatographed on a silica gel column using 10% ethyl acetate-benzene as the eluate. Fractions 1 through 16, comprised of 10-25 ml. each, and containing p-fluorobromobenzene, are collected and discarded. Fractions 16 to 38 are combined and concentrated in vacuo to an oil which solidifies on standing at 5° C. overnight. The product, 3.5 g. (76% yield), is triturated with pentane and filtered. The analytical sample is recrystallized from pentane, m.p. 118°–120° C.

Anal. Calc'd for $C_{20}H_{18}O_2N_2F_2$: C, 67.4; H, 5.1; N, 7.9. Found: C, 67.4; H, 5.2; N, 7.8.

C. 8-fluoro-5-(p-fluorophenyl)-1,2,3,4-tetrahydro-γ-carboline

A suspension of 3.56 g. (0.01 mole) of 8-fluoro-5-(p-fluorophenyl)-2-carbethoxy-1,2,3,4-tetrahydro-γ-carboline and 8.2 g. (0.146 mole) of potassium hydroxide in 53 ml. of ethanol containing 5 ml. of water is heated to reflux overnight. An additional 3.0 g. of potassium hydroxide is added and the heating continued for 23 hrs. The brownish solution is cooled, concentrated in vacuo to dryness and partitioned between water and diethyl ether. The aqueous layer is further extracted with ether, and the ether layers combined, washed with a saturated brine solution and dried over magnesium sulfate. Removal of the solvent provides the desired product as an orange solid, 2.6 g. m.p. 125°–127° C. The analytical sample is recrystallized from pentane, m.p. 127°–128° C.

Anal. Calc'd for $C_{17}H_{14}N_2F_2$: C, 71.8; H, 5.0; N, 9.9. Found: C, 71.6; H, 5.1; N, 10.2.

The hydrochloride salt is prepared by bubbling hydrogen chloride into a solution of the free base in diethyl ether, m.p. 270°–272° C.

EXAMPLE 2

Starting with the appropriate phenylhydrazine and employing the procedures of Example 1, the following 5-aryl-1,2,3,4-tetrahydro-γ-carbolines are prepared as the free base and hydrochloride salts: 8-chloro-5-(p-fluorophenyl)-1,2,3,4-tetrahydro-γ-carboline hydrochloride, m.p. 269°–271° C.; 8-bromo-5-phenyl-1,2,3,4-tetrahydro-γ-carboline hydrochloride, m.p. 280°–282° C.; 8-methyl-5-phenyl-1,2,3,4-tetrahydro-γ-carboline hydrochloride, m.p. 288°–289° C.; 8-fluoro-5-(p-chlorophenyl)-1,2,3,4-tetrahydro-γ-carboline hydrochloride, m.p. 283°–285° C.; 8-chloro-5-phenyl-1,2,3,4-tetrahydro-γ-carboline hydrochloride, m.p. 276°–278° C.; 8-fluoro-5-(m-fluorophenyl)-1,2,3,4-tetrahydro-γ-carboline hydrochloride, m.p. 237°–238° C.; and 8-fluoro-5-(o-fluorophenyl)-1,2,3,4-tetrahydro-γ-carboline hydrochloride, m.p. 176°–178° C.; and as the free base: 8-fluoro-5-(p-anisyl)-1,2,3,4-tetrahydro-γ-carboline, m.p. 119°–122° C.; 8-chloro-5-(p-chlorophenyl)-1,2,3,4-tetrahydro-γ-carboline; 8-bromo-5-(p-fluorophenyl)-1,2,3,4-tetrahydro-γ-carboline; 8-methyl-5-(p-chlorophenyl)-1,2,3,4-tetrahydro-γ-carboline; 5-(p-fluorophenyl)-1,2,3,4-tetrahydro-γ-carboline; 5-(p-chlorophenyl)-1,2,3,4-tetrahydro-γ-carboline; 8-chloro-5-(m-fluorophenyl)-1,2,3,4-tetrahydro-γ-carboline; 8-chloro-5-(o-chlorophenyl)-1,2,3,4-tetrahydro-γ-carboline; 8-bromo-5-(m-chlorophenyl)-1,2,3,4-tetrahydro-γ-carboline; 8-bromo-5-(m-fluorophenyl)-1,2,3,4-tetrahydro-γ-carboline; 8-fluoro-5-(o-anisyl)-1,2,3,4-tetrahydro-γ-carboline; 8-fluoro-5-(m-anisyl)-1,2,3,4-tetrahydro-γ-carboline; 5-(o-fluorophenyl)-1,2,3,4-tetrahydro-γ-carboline; 5-(m-chlorophenyl)-1,2,3,4-tetrahydro-γ-carboline; 5-(m-anisyl)-1,2,3,4-tetrahydro-γ-carboline; 8-bromo-5-(m-anisyl)-1,2,3,4-tetrahydro-γ-carboline; 8-chloro-5-(o-anisyl)-1,2,3,4-tetrahydro-γ-carboline; 8-fluoro-5-(m-chlorophenyl)-1,2,3,4-tetrahydro-γ-carboline; and 8-fluoro-5-(o-chlorophenyl)-1,2,3,4-tetrahydro-γ-carboline.

EXAMPLE 3

8-Fluoro-5-(p-fluorophenyl)-2-(β-phenethyl)-1,2,3,4-tetrahydro-γ-carboline hydrochloride To a stirred suspension of 1.4 g. (4.9 m moles) of 8-fluoro-5-(p-fluorophenyl)-1,2,3,4-tetrahydro-γ-carboline and 1.02 g. (7.4 m moles) of potassium carbonate in 10 ml. of dimethylformamide, heated to 60° C. is added dropwise 1.09 g. (5.9 m moles) of β-phenethyl bromide in 10 ml. of the same solvent. After heating for 3.5 hrs., the reaction mixture is decanted into 200 ml. of an aqueous 2% potassium carbonate solution, and the resulting solution subsequently extracted (3 × 200 ml.) with benzene. The combined extracts are washed successively with water and a saturated brine solution, and dried over magnesium sulfate. The solvent is removed in vacuo and the residual oil which crystallizes on standing is triturated with hexane and filtered, 1.6 g., m.p. 115°–121° C.

The crude product is chromatographed on a silica-gel column using 25% ethyl acetate-75% benzene as the eluate. Fractions 12–32, comprising 5–7 ml. per fraction, are collected and evaporated to dryness. The residual crystalline product is dissolved in diethyl ether-methylene chloride and converted to the hydrochloride salt using gaseous hydrogen chloride, 1.13 g. (54% yield), m.p. 275°–276° C.

Anal. Calc'd for $C_{25}H_{22}N_2F_2 \cdot HCl$: C, 70.7; H, 5.5; N, 6.6. Found: C, 70.4; H, 5.5; N, 6.5.

EXAMPLE 4

The procedure of Example 3 is repeated, starting with the appropriate alkylating agent and requisite 5-aryl-1,2,3,4-tetrahydro-γ-carboline, to provide the following analogs as the hydrochloride salt:

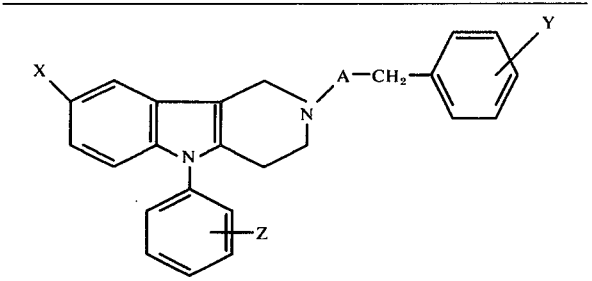

| X | Z | A | Y |
|---|---|---|---|
| F— | p-F— | —CH₂— | p-Cl— |
| F— | p-F— | —CH₂— | p-H— |
| F— | p-F— | —(CH₂)₃— | p-F— |
| F— | p-F— | —(CH₂)₅— | p-F— |
| F— | p-Cl— | —CH₂— | p-Cl— |
| F— | p-Cl— | —(CH₂)₃— | p-F— |
| F— | p-Cl— | —(CH₂)₄— | p-Cl— |
| F— | p-H— | —(CH₂)₃— | p-F— |
| Cl— | p-H— | —CH₂— | p-H— |
| Cl— | p-H— | —(CH₂)₃— | p-H— |
| Cl— | p-F— | —(CH₂)₃— | p-F— |
| Cl— | p-F— | —(CH₂)₅— | p-F— |
| Cl— | p-Cl— | —CH₂— | p-Cl— |
| Cl— | p-Cl— | —CH₂— | p-H— |
| Br— | p-Cl— | —(CH₂)₄— | p-Cl— |
| Br— | p-F— | —(CH₂)₃— | p-F— |
| Br— | p-F— | —CH₂— | p-H— |
| Br— | p-H— | —CH₂— | p-Cl— |
| CH₃— | p-H— | —CH₂— | p-H— |
| CH₃— | p-H— | —(CH₂)₂— | p-H— |
| CH₃— | p-H— | —(CH₂)₃— | p-F— |
| CH₃— | p-F— | —(CH₂)₃— | p-F— |
| CH₃— | p-F— | —CH₂— | p-H— |
| H— | p-F— | —(CH₂)₃— | p-F— |
| H— | p-F— | —CH₂— | p-F— |
| H— | p-F— | —(CH₂)₄— | p-Cl— |
| H— | p-Cl— | —CH₂— | P-H— |
| H— | p-Cl— | —(CH₂)₃— | p-F— |
| F— | o-F— | —CH₂— | H— |
| F— | o-F— | —(CH₂)₂— | m-Cl— |
| F— | m-F— | —(CH₂)₅— | o-F— |
| F— | o-CH₃O— | —(CH₂)₃— | H— |
| F— | p-F— | —(CH₂)₃— | m-Cl— |
| F— | o-Cl— | —CH₂— | m-F— |
| Cl— | m-F— | —(CH₂)₂— | m-Cl— |
| Cl— | m-F— | —(CH₂)₃— | o-Cl— |
| Cl— | o-F— | —(CH₂)₃— | H— |
| Cl— | o-Cl— | —CH₂— | o-Cl— |
| Cl— | o-CH₃O— | —(CH₂)₄— | m-F— |
| Cl— | p-F— | —(CH₂)₄— | m-F— |
| Br— | m-Cl— | —CH₂— | o-F— |
| Br— | p-F— | —(CH₂)₂— | o-F— |
| Br— | m-F— | —(CH₂)₃— | o-F— |
| Br— | m-CH₃O— | —(CH₂)₃— | m-CH₃— |
| Br— | m-CH₃O— | —(CH₂)₃— | p-CH₃— |
| H— | o-F— | —(CH₂)₂— | m-Cl— |
| H— | o-F— | —(CH₂)₃— | m-F— |
| H— | m-Cl— | —(CH₂)₃— | H— |
| H— | m-CH₃O— | —(CH₂)₅— | p-F— |

EXAMPLE 5

8-Fluoro-5-(p-fluorophenyl)-2-[3-(p-fluorobenzoyl)-propyl]-1,2,3,4-tetrahydro-γ-carboline hydrochloride In a manner similar to Example 3, 2.84 g. (0.01 mole) of 8-fluoro-5-(p-fluorophenyl)-1,2,3,4-tetrahydro-γ-carboline, 2.8 g. (0.01 mole) of ω-chloro-p- fluorobutyrophenone, 3.15 g. (0.03 mole) of sodium carbonate and a trace (50 mg.) of potassium iodide in 50 ml. of 4-methyl-2-pentanone gave, after heating to reflux for 15 hrs. followed by work-up, 2.6 g. of the desired product as the free base, m.p. 150°–155° C.

The crude base in diethyl ether is converted to the hydrochloride using hydrogen chloride gas, 2.72 g., m.p. 235° C., dec. Recrystallization from ethanol containing a small amount of diethyl ether gives the pure product, 2.2 g., m.p. 237°–238° C.

Anal. Calc'd for $C_{27}H_{23}ON_2F_3 \cdot HCl \cdot \frac{1}{4} H_2O$: C, 66.3; H, 4.9; N, 5.7. Found: C, 66.3; H, 5.2; N, 5.6.

EXAMPLE 6

Employing an alkylation procedure similar to that of Examples 3, 4 and 5, and starting with the appropriate alkylating agent and 1,2,3,4-tetrahydro-γ-carboline, the following analogs are prepared:

8-fluoro-5-(p-fluorophenyl)-2-[2-(p-fluorobenzoyl)ethyl]-1,2,3,4-tetrahydro-γ-carboline hydrochloride, m.p. 195°–198° C.

Anal. Calc'd for $C_{26}H_{21}ON_2F_3 \cdot HCl \cdot \frac{1}{3} H_2O$: C, 65.6; H, 4.7; N, 5.9. Found: C, 65.6; H, 4.7; N, 5.9;

8-fluoro-5-(p-fluorophenyl)-2-[4-(p-fluorobenzoyl)butyl]-1,2,3,4-tetrahydro-γ-carboline hydrochloride, m.p. 242°–244° C.

Anal. Calc'd for $C_{28}H_{25}ON_2F_3 \cdot HCl \cdot \frac{1}{4} H_2O$: C, 66.8; H, 5.3; N, 5.6. Found: C, 66.8; H, 5.3; N, 5.5;

8-fluoro-5-(p-fluorophenyl)-2-(3-benzoylpropyl)-1,2,3,4-tetrahydro-γ-carboline hydrochloride, m.p. 208°–211° C.

Anal. Calc'd for $C_{27}H_{24}ON_2F_2 \cdot HCl \cdot H_2O$: C, 66.9; H, 5.6; N, 5.8. Found: C, 67.2; H, 5.4; N, 5.8;

8-fluoro-5-(p-fluorophenyl)-2-[3-(p-toluoyl)propyl]-1,2,3,4-tetrahydro-γ-carboline, m.p. 125°–127° C.

Anal. Calc'd for $C_{28}H_{26}ON_2F_3 \cdot \frac{1}{4} H_2O$: C, 74.9; H, 5.8; N, 6.2. Found: C, 74.6; H, 6.0; N, 6.0.

8-fluoro-5-(p-fluorophenyl)-2-[3-(p-chlorobenzoyl)propyl]-1,2,3,4-tetrahydro-γ-carboline hydrochloride, m.p. 201°–203° C.

Anal. Calc'd for $C_{27}H_{23}ON_2ClF_2$ (free base): C, 69.7; H, 5.0; N, 6.0. Found: C, 69.4; H, 5.0; N, 5.9;

8-fluoro-5-(p-trifluoromethylphenyl)-2-[3-(p-fluorobenzoyl)propyl]-1,2,3,4-tetrahydro-γ-carboline hydrochloride, m.pl 245°–247° C.

Anal. Calc'd for $C_{28}H_{23}ON_2F_5 \cdot HCl$: C, 62.9; H, 4.5; N, 5.5. Found: C, 62.5; H, 4.5; N, 5.2;

8-fluoro-5-(m-trifluoromethylphenyl)-2-[3-(p-fluorobenzoyl)propyl]-1,2,3,4-tetrahydro-γ-carboline hydrochloride, m.p. 247°–248° C.

Anal. Calc'd for $C_{28}H_{23}ON_2F_5 \cdot HCl \cdot \frac{1}{3} H_2O$: 62.2; H, 4.6; N, 5.2. Found: 62.2; H, 4.5; N, 5.2;

8-fluoro-5-(p-methoxyphenyl)-2-[3-(p-fluorobenzoyl)propyl]-1,2,3,4-tetrahydro-γ-carboline hydrochloride, m.p. 209°–211° C.

Anal. Calc'd for $C_{28}H_{26}O_2N_2F_2 \cdot HCl \cdot \frac{1}{4} H_2O$: C, 67.1; H, 5.5; N, 5.6. Found: C, 67.3; H, 5.3; N, 5.5;

8-chloro-5-(p-fluorophenyl)-2-[3-(p-fluorobenzoyl)propyl]-1,2,3,4-tetrahydro-γ-carboline hydrochloride, m.p. 233°–235° C.

Anal. Calc'd for $C_{27}H_{23}ON_2ClF_2 \cdot HCl$: C, 64.7; H, 4.8; N, 5.6. Found: C, 64.3; H, 4.8; N, 5.7.

8-fluoro-5-(m-fluorophenyl)-2-[3-(p-fluorobenzoyl)propyl]-1,2,3,4-tetrahydro-γ-carboline hydrochloride, m.p. 205°–208° C.

Anal. Calc'd for $C_{27}H_{23}ON_2F_3 \cdot HCl \cdot \frac{1}{2} H_2O$: C, 65.7; H, 5.1; N, 5.7. Found: C, 65.8; H, 5.1; N, 5.6.

8-fluoro-5-(o-fluorophenyl)-2-[3-(p-fluorobenzoyl)propyl]-1,2,3,4-tetrahydro-γ-carboline hydrochloride, m.p. 203°–205° C.

Anal. Calc'd for $C_{27}H_{23}ON_2F_3 \cdot HCl \cdot \frac{1}{3} H_2O$: C, 65.3; H, 5.2; N, 5.6. Found: C, 65.3; H, 5.0; N, 5.6.

8-fluoro-5-(p-fluorophenyl)-2-[3-(m-fluorobenzoyl)propyl]-1,2,3,4-tetrahydro-γ-carboline hydrochloride, m.p. 207°–209° C.

Anal. Calc'd for $C_{27}H_{23}ON_2F_3 \cdot HCl$: C, 66.3; H, 4.9; N, 5.7. Found: C, 66.4; H, 5.1; N, 5.5.

EXAMPLE 7

Again, repeating the alkylation procedure of Examples 3, 4, 5 and 6, and starting with the requisite reagents, the following compounds are prepared:

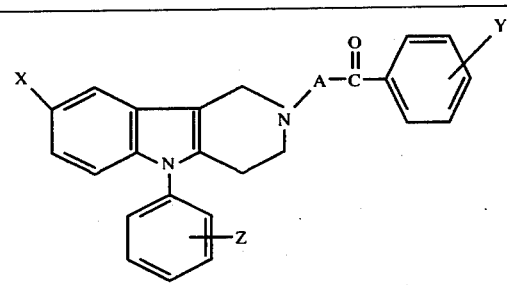

| X | Z | A | Y |
|---|---|---|---|
| F— | p-F— | —(CH₂)₅— | p-F— |
| F— | p-F— | —CH₂— | p-Cl— |
| F— | p-Cl— | —(CH₂)₃— | p-F— |
| F— | p-Cl— | —(CH₂)₃— | p-Cl— |
| F— | p-Cl— | —(CH₂)₃— | p-CH₃— |
| F— | p-OCH₃— | —(CH₂)₂— | p-F— |
| F— | p-OCH₃— | —(CH₂)₂— | p-H— |
| F— | p-OCH₃— | —(CH₂)₃— | p-Cl— |
| F— | p-H— | —(CH₂)₃— | p-F— |
| Cl— | p-F— | —CH₂— | p-Cl— |
| Cl— | p-F— | —(CH₂)₃— | p-Cl— |
| Cl— | p-F— | —(CH₂)₃— | p-CH₃— |
| Cl— | p-H— | —(CH₂)₃— | p-F— |
| Cl— | p-H— | —(CH₂)₅— | p-F— |
| Cl— | p-Cl— | —(CH₂)₃— | p-F— |
| Cl— | p-OCH₃— | —(CH₂)₃— | p-F— |
| Cl— | p-OCH₃— | —(CH₂)₃— | p-CH₃— |
| Br— | p-H— | —(CH₂)₃— | p-F— |
| Br— | p-H— | —(CH₂)₃— | p-H— |
| Br— | p-H— | —(CH₂)₄— | p-F— |
| Br— | p-OCH₃— | —(CH₂)₂— | p-F— |
| Br— | p-OCH₃— | —(CH₂)₃— | p-F— |
| Br— | p-F— | —(CH₂)₃— | p-F— |
| Br— | p-Cl— | —(CH₂)₂— | p-F— |
| CH₃— | p-Cl— | —(CH₂)₃— | p-CH₃— |
| CH₃— | p-Cl— | —(CH₂)₅— | p-H— |
| CH₃— | p-F— | —(CH₂)₃— | p-F— |
| CH₃— | p-OCH₃— | —(CH₂)₃— | p-F— |
| CH₃— | p-OCH₃— | —(CH₂)₄— | p-F— |
| CH₃— | p-H— | —(CH₂)₃— | p-CH₃— |
| H— | p-OCH₃— | —(CH₂)₃— | p-F— |
| H— | p-OCH₃— | —(CH₂)₃— | p-Cl— |
| H— | p-OCH₃— | —(CH₂)₂— | p-CH₃— |
| H— | p-OCH₃— | —(CH₂)₅— | p-H— |
| H— | p-Cl— | —(CH₂)₃— | p-F— |
| H— | p-Cl— | —(CH₂)₅— | p — |
| F— | o-F— | —(CH₂)₃— | p-F— |
| F— | o-F— | —(CH₂)₃— | m-F— |
| F— | m-F— | —(CH₂)₄— | m-F— |
| F— | p-F— | —(CH₂)₃— | o-F— |
| F— | m-Cl— | —CH₂— | m-F— |
| Cl— | p-F— | —(CH₂)₃— | o-F— |
| Cl— | m-F— | —(CH₂)₂— | o-Cl— |
| Cl— | o-CH₃O— | —(CH₂)₃— | m-Cl— |
| Cl— | o-Cl— | —(CH₂)₂— | m-CH₃— |
| Cl— | m-F— | —(CH₂)₅— | m-CH₃— |
| Cl— | o-CH₃O— | —CH₂— | o-CH₃— |
| Br— | p-F— | —(CH₂)₃— | m-Cl— |
| Br— | m-Cl— | —CH₂— | o-CH₃— |
| Br— | m-F— | —(CH₂)₄— | m-F— |
| Br— | m-CH₃O— | —(CH₂)₃— | o-F— |
| Br— | m-F— | —(CH₂)₃— | o-CH₃— |
| Br— | m-Cl— | —(CH₂)₃— | o-F— |
| H— | p-F— | —(CH₂)₃— | o-F— |

-continued

| X | Z | A | Y |
|---|---|---|---|
| H— | p-F— | —(CH$_2$)$_3$— | m-Cl— |
| H— | o-F— | —(CH$_2$)$_3$— | p-F— |
| H— | m-Cl— | —(CH$_2$)$_4$— | m-CH$_3$— |
| H— | m-Cl— | —CH$_2$— | m-F— |
| H— | m-CH$_3$O— | —(CH$_2$)$_2$— | m-Cl— |
| H— | m-CH$_3$O— | —(CH$_2$)$_4$— | m-F |

EXAMPLE 8

8-Chloro-5-(p-fluorophenyl)-2-[4-(p-fluorophenyl)-4-hydroxybutyl]-1,2,3,4-tetrahydro-γ-carboline hydrochloride To 575 mg. (15.2 m moles) of sodium borohydride in 25 ml. of ethanol is added dropwise 1.8 g.(3.8 m moles) of 8-chloro-5-(p-fluorophenyl)-2-[3-(p-fluorobenzoyl)propyl]-1,2,3,4-tetrahydro-γ-carboline in a warm solution of 40 ml. of ethanol and 10 ml. of tetrahydrofuran at such a rate that a gentle reflux is maintained. After the addition is complete the reaction is heated to reflux for an additional hour and is then cooled to room temperature. The supernatant is decanted into 200 ml. of water and organic solvents are removed from the aqueous solution in vacuo. The residual water is extracted (3 × 75 ml.) with methylene chloride, and the organic layers combined, back-washed with a saturated brine solution and dried over magnesium sulfate. The solvent is removed under reduced pressure and the residual product is dissolved in diethyl ether-methylene chloride. Hydrogen chloride gas is carefully bubbled into the solution until a precipitate ceases to form. The desired product is filtered and dried, 1.9 g., m.p. 245°–246° C.

Anal. Calc'd for C$_{27}$H$_{25}$ON$_2$ClF$_2$·HCl·H$_2$O: C, 62.2; H, 5.4; N, 5.4. Found: C, 62.3; H, 5.1; N, 5.3.

EXAMPLE 9

The reduction procedure of Example 8 is repeated, starting with the appropriate ketone, to provide the following γ-carbolines:

8-fluoro-5-(p-methoxyphenyl)-2-[4-(p-fluorophenyl)-4-hydroxybutyl]-1,2,3,4-tetrahydro-γ-carboline hydrochloride, m.p. 235°–236° C.

Anal. Calc'd for C$_{28}$H$_{28}$O$_2$N$_2$F$_2$·HCl: C, 67.4; H, 5.9; N, 5.6. Found: C, 67.7; H, 5.8; N, 5.6;

8-fluoro-5-(m-trifluoromethylphenyl)-2-[4-(p-fluorophenyl)-4-hydroxybutyl]-1,2,3,4-tetrahydro-γ-carboline hydrochloride, m.p. 243°–245° C.

Anal. Calc'd for C$_{28}$H$_{25}$ON$_2$F$_5$·HCl·½ H$_2$O: C, 61.6; H, 5.0; N, 5.1. Found: C, 61.6; H, 4.8; N, 5.1;

8-fluoro-5-(p-fluorophenyl)-2-[4-(p-tolyl)-4-hydroxybutyl]-1,2,3,4-tetrahydro-γ-carboline hydrochloride, m.p. 236°–237° C.

Anal. Calc'd for C$_{28}$H$_{28}$ON$_2$F$_2$·HCl·½ H$_2$O: C, 68.3; H, 6.1; N, 5.7. Found: C, 68.7; H, 6.3; N, 5.6.

8-fluoro-5-(p-fluorophenyl)-2-[4-(p-chlorophenyl)-4-hydroxybutyl]-1,2,3,4-tetrahydro-γ-carboline hydrochloride, m.p. 242°–244° C.

Anal. Calc'd for C$_{27}$H$_{25}$ON$_2$F$_2$Cl·HCl·¾ H$_2$O: C, 62.7; H, 5.1; N, 5.4. Found: C, 62.7; H, 5.1; N, 5.3;

8-fluoro-5-(p-fluorophenyl)-2-[4-(m-trifluoromethylphenyl)-4-hydroxybutyl]-1,2,3,4-tetrahydro-γ-carboline hydrochloride, m.p. 225°–227° C.

Anal. Calc'd for C$_{28}$H$_{25}$ON$_2$F$_5$·HCl·¼ H$_2$O: C, 62.2; H, 4.7; N, 5.2. Found: C, 62.2; H, 4.9; N, 5.2;

8-fluoro-5-(p-fluorophenyl)-2-[3-(p-fluorophenyl)-4-hydroxypropyl]-1,2,3,4-tetrahydro-γ-carboline hydrochloride, m.p. 237°–239° C.

Anal. Calc'd for C$_{26}$H$_{23}$ON$_2$F$_3$·HCl: C, 66.0; H, 5.1; N, 5.9. Found: C, 65.8; H, 5.1; N, 5.9;

8-fluoro-5-(p-fluorophenyl)-2-[4-(p-fluorophenyl)-4-hydroxybutyl]-1,2,3,4-tetrahydro-γ-carboline hydrochloride, m.p. 249°–250° C.

Anal. Calc'd for C$_{27}$H$_{25}$ON$_2$F$_3$·HCl·½ H$_2$O: C, 65.4; H, 5.5; N, 5.6. Found: C, 65.6; H, 5.4; N, 5.6;

8-fluoro-5-(p-fluorophenyl)-2-(4-phenyl-4-hydroxybutyl)-1,2,3,4-tetrahydro-γ-carboline hydrochloride, m.p. 236°–238° C.

Anal. Calc'd for C$_{27}$H$_{26}$ON$_2$F$_2$·HCl·½ H$_2$O: C, 68.0; H, 5.7; N, 5.9. Found: C, 67.7; H, 5.8; N, 5.8;

8-fluoro-5-(p-fluorophenyl)-2-[4-(4-chloro-3-trifluoromethylphenyl)-4-hydroxybutyl]-1,2,3,4-tetrahydro-γ-carboline hydrochloride, m.p. 216°–217° C.

Anal. Calc'd for C$_{28}$H$_{24}$ON$_2$F$_5$Cl·HCl: C, 58.9; H, 4.4; N, 5.0. Found: C, 58.7; H, 4.3; N, 5.0;

8-fluoro-5-(p-fluorophenyl)-2-[5-p-fluorophenyl)-5-hydroxypentyl]-1,2,3,4-tetrahydro-γ-carboline hydrochloride, m.p. 207°–208° C.

Anal. Calc'd for C$_{28}$H$_{27}$ON$_2$F$_3$·HCl·¾ H$_2$O: C, 65.4; H, 5.8; N, 5.4. Found: C, 65.2; H, 5.6; N, 5.4.

8-fluoro-5-(o-fluorophenyl)-2-[4-(p-fluorophenyl)-4-hydroxybutyl]-1,2,3,4-tetrahydro-γ-carboline hydrochloride, m.p. 229°–231° C.

Anal. Calc'd for C$_{27}$H$_{25}$ON$_2$F$_3$·HCl: C, 66.5; H, 5.4; N, 5.7. Found: C, 66.8; H, 5.5; N, 5.8.

8-fluoro-5-(m-fluorophenyl)-2-[4-(p-fluorophenyl)-4-hydroxybutyl]-1,2,3,4-tetrahydro-γ-carboline hydrochloride, m.p. 234°–235° C.

Anal. Calc'd for C$_{27}$H$_{25}$ON$_2$F$_3$·HCl: C, 66.5; H, 5.4; N, 5.7. Found: C, 66.8; H, 5.4; N, 5.7.

8-fluoro-5-(p-fluorophenyl)-2-[4-(m-fluorophenyl)-4-hydroxybutyl]-1,2,3,4-tetrahydro-γ-carboline hydrochloride, m.p. 228°–230° C.

Anal. Calc'd for C$_{27}$H$_{25}$ON$_2$F$_3$·HCl·¼ H$_2$O: C, 66.0; H, 5.3; N, 5.7. Found: C, 65.7; H, 5.6; N, 5.7.

EXAMPLE 10

Starting with the ketones of Examples 6 and 7 and employing the procedures of Example 8, the following carbinols are synthesized:

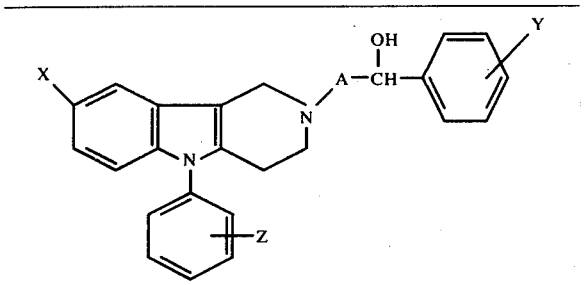 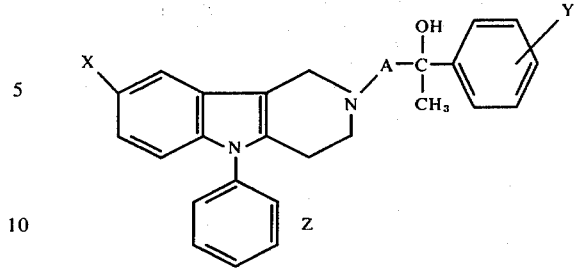

| X | Z | A | Y |
|---|---|---|---|
| F— | p-F— | —(CH₂)₅— | p-F— |
| F— | p-F— | —CH₂— | p-Cl— |
| F— | p-CH₃O— | —(CH₂)₂— | H— |
| F— | p-Cl— | —(CH₂)₂— | p-Cl— |
| F— | o-F— | —(CH₂)₃— | p-F— |
| F— | m-F— | —(CH₂)₄— | m-F— |
| F— | m-Cl— | —CH₂— | m-F— |
| Cl— | p-F— | —CH₂— | p-Cl— |
| Cl— | p-F— | —(CH₂)₃— | p-Cl— |
| Cl— | H— | —(CH₂)₅— | p-F— |
| Cl— | p-CH₃O— | —(CH₂)₃— | p-F— |
| Cl— | p-F— | —(CH₂)₃— | o-F— |
| Cl— | m-F— | —(CH₂)₂— | o-Cl— |
| Cl— | o-CH₃O— | —(CH₂)₃— | m-Cl— |
| Cl— | m-F— | —(CH₂)₅— | m-CH₃— |
| Br— | H— | —(CH₂)₃— | p-F— |
| Br— | p-CH₃O— | —(CH₂)₂— | p-F— |
| Br— | p-Cl— | —(CH₂)₂— | p-F— |
| Br— | p-F— | —(CH₂)₃— | m-Cl— |
| Br— | m-Cl— | —CH₂— | o-CH₃— |
| Br— | m-CH₃O— | —(CH₂)₃— | o-F— |
| Br— | m-F— | —(CH₂)₃— | o-CH₃— |
| H— | p-CH₃O— | —(CH₂)₅— | H— |
| H— | p-CH₃O— | —(CH₂)₃— | p-F— |
| H— | p-Cl— | —(CH₂)₃— | p-F— |
| H— | p-F— | —(CH₂)₃— | o-F— |
| H— | p-F— | —(CH₂)₃— | m-Cl— |
| H— | m-Cl— | —(CH₂)₄— | m-CH₃— |
| H— | m-CH₃O— | —(CH₂)₂— | m-Cl— |
| H— | m-CH₃O— | —(CH₂)₄— | m-F— |

EXAMPLE 11

8-Fluoro-5-(p-fluorophenyl)-2-[4-(p-fluorophenyl)-4-hydroxypentyl]-1,2,3,4-tetrahydro-γ-carboline hydrochloride A solution of 3.3 g. (7.3 m moles) of 8-fluoro-5-(p-fluorophenyl)-2-[3-(p-fluorobenzoyl)propyl]-1,2,3,4-tetrahydro-γ-carboline in 15 ml. of tetrahydrofuran is added dropwise to a cooled solution of methyl magnesium iodide in 30 ml. of diethyl ether, prepared from 4.56 g. (32.2 m moles) of methyl iodide and 788 mg. (32.2 m moles) of magnesium metal, and the resulting reaction mixture allowed to stir overnight at room temperature. The mixture is decanted into 150 ml. of ice-water, and the organic solvent removed from solution in vacuo. The aqueous solution is extracted (3 × 75 ml.) with methylene chloride and the organic extracts combined, dried over magnesium sulfate and concentrated under reduced pressure to a yellow oil. The residual product in diethyl ether is converted to the hydrochloride using hydrogen chloride gas. The resulting precipitated product is filtered and dried, 1.35 g., m.p. 216°–217° C.

Anal. Calc'd for $C_{28}H_{27}ON_2F_3·HCl·⅓ H_2O$: C, 66.3; H, 5.6; N, 5.5 Found: C, 66.6; H, 5.7; N, 5.6.

EXAMPLE 12

Starting with methyl magnesium iodide and the 5-aryl-2-benzoylalkyl-1,2,3,4-tetrahydro-γ-carbolines of Examples 6 and 7 and employing the procedure of Example 11, the following congeners are prepared:

| X | Z | A | Y |
|---|---|---|---|
| F— | p-F— | —(CH₂)₅— | p-F— |
| F— | p-F— | —(CH₂)₄— | p-CH₃— |
| F— | p-Cl— | —(CH₂)₃— | p-F— |
| F— | p-Cl— | —(CH₂)₃— | p-Cl— |
| F— | p-CH₃O— | —(CH₂)₅— | H— |
| F— | o-F— | —(CH₂)₃— | p-F— |
| F— | m-F— | —(CH₂)₄— | m-F— |
| F— | m-Cl— | —CH₂— | m-F— |
| Cl— | p-F— | —CH₂— | p-Cl— |
| Cl— | p-F— | —(CH₂)₃— | p-Cl— |
| Cl— | H— | —(CH₂)₅— | p-F— |
| Cl— | p-CH₃O— | —(CH₂)₃— | p-CH₃— |
| Cl— | p-F— | —(CH₂)₃— | o-F— |
| Cl— | m-F— | —(CH₂)₂— | o-Cl— |
| Cl— | o-CH₃O— | —(CH₂)₃— | m-Cl— |
| Cl— | m-F— | —(CH₂)₅— | m-CH₃— |
| Cl— | o-CH₃O— | —CH₂— | o-CH₃— |
| Br— | H— | —(CH₂)₃— | p-F— |
| Br— | p-CH₃O— | —(CH₂)₂— | p-F— |
| Br— | p-F— | —(CH₂)₃— | p-F— |
| Br— | p-F— | —(CH₂)₃— | m-Cl— |
| Br— | m-Cl— | —CH₂— | o-CH₃— |
| Br— | m-F— | —(CH₂)₄— | m-F— |
| Br— | m-CH₃O— | —(CH₂)₃— | o-F— |
| Br— | m-F— | —(CH₂)₃— | o-CH₃— |
| Br— | m-Cl— | —(CH₂)₃— | o-F— |
| H— | p-CH₃O— | —(CH₂)₃— | p-F— |
| H— | p-CH₃O— | —(CH₂)₂— | p-CH₃— |
| H— | p-Cl— | —(CH₂)₃— | p-F— |
| H— | p-Cl— | —(CH₂)₅— | H— |
| H— | p-F— | —(CH₂)₃— | o-F— |
| H— | p-F— | —(CH₂)₃— | m-Cl— |
| H— | o-F— | —(CH₂)₃— | p-F— |
| H— | m-Cl— | —CH₂— | m-F— |
| H— | m-CH₃O— | —(CH₂)₂— | m-Cl— |
| H— | m-CH₃O— | —(CH₂)₄— | m-F— |

EXAMPLE 13

8-Fluoro-5-(p-fluorophenyl)-2-[4-(p-fluorophenyl)-4-acetoxybutyl]-1,2,3,4-tetrahydro-γ-carboline Acetyl chloride (260 mg., 3.3 m moles) in 10 ml. of methylene chloride is added dropwise to a cold solution of 1.0 g. (2.2 m moles) of 8-fluoro-5-(p-fluorophenyl)-2-[4-(p-fluorophenyl)-4-hydroxybutyl]-1,2,3,4-tetrahydro-γ-carboline in 30 ml. of methylene chloride containing 350 mg. (4.4 m moles) of pyridine. Following the addition the reaction mixture is allowed to warm to room temperature and stir overnight. The mixture is decanted into a cold saturated aqueous sodium bicarbonate solution, and the crude product is extracted (3 × 50 ml.) with methylene chloride. The combined organic extracts are dried over magnesium sulfate and concentrated to an oil, which on chromatographing on a silica gel column, using 1:1 benzene-ethyl acetate as an eluate, provides the purified product in fractions 4–7 as a yellow oil, 392 mg.

Anal. Calc'd for $C_{29}H_{27}O_2N_2F_3$: C, 70.7; H, 5.5; N, 5.9. Found: C, 70.6; H, 5.4; N, 5.8.

In a similar manner are prepared:

8-Fluoro-5-(p-fluorophenyl)-2-[4-(p-fluorophenyl)-4-n-heptanoyloxybutyl]-1,2,3,4-tetrahydro-γ-carboline hydrochloride, m.p. 171°–173° C.; 8-fluoro-5-(p- fluorophenyl)-2-[4-(p-fluorophenyl)-4-n-nonanoyloxybutyl]-1,2,3,4-tetrahydro-γ-carboline hydrochloride, m.p. 138°-139° C.; and 8-fluoro-5-(p-fluorophenyl)-2-[4-(p-fluorophenyl)-4-n-valeryloxybutyl]-1,2,3,4-tetrahydro-γ-carboline hydrochloride, m.p. 175°-179° C.

EXAMPLE 14

Starting with the appropriate carbinol from Examples 8 through 12, and the requisite acid chloride or anhydride, and employing the procedure of Example 13, the following esters are synthesized:

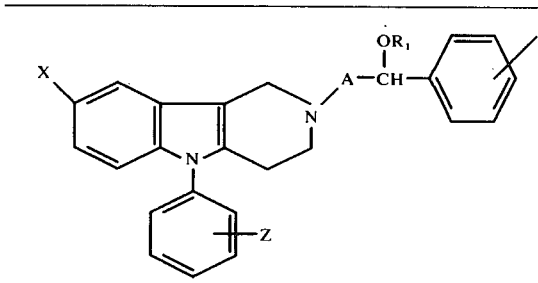

| X | Z | A | R₁ | Y |
|---|---|---|---|---|
| F— | p-CH₃O— | —(CH₂)₃— | CH₃CO— | p-F— |
| F— | p-F— | —(CH₂)₃— | (CH₃)₃CCO— | p-CH₃— |
| F— | p-F— | —(CH₂)₄— | CH₃CO— | p-F— |
| F— | p-F— | —(CH₂)₄— | CH₃(CH₂)₇CO— | p-F— |
| F— | p-Cl— | —(CH₂)₃— | CH₃CO— | p-Cl— |
| F— | o-F— | —(CH₂)₃— | CH₃(CH₂)₆CO— | p-F— |
| F— | m-F— | —(CH₂)₄— | CH₃(CH₂)₂CO— | m-F— |
| F— | m-Cl— | —CH₂— | CH₃CO— | m-F— |
| Cl— | p-F— | —(CH₂)₃— | (CH₃)₂CHCO— | p-F— |
| Cl— | H— | —(CH₂)₅— | CH₃CO— | p-F— |
| Cl— | p-CH₃O— | —(CH₂)₃— | CH₃CO— | p-CH₃— |
| Cl— | p-Cl— | —(CH₂)₃— | CH₃(CH₂)₃CO— | p-F— |
| Cl— | m-F— | —(CH₂)₂— | CH₃(CH₂)₇CO— | o-Cl— |
| Cl— | o-CH₃O— | —(CH₂)₃— | CH₃(CH₂)₅CO— | m-Cl— |
| Cl— | m-F— | —(CH₂)₅— | (CH₃)₂CHCO— | m-CH₃— |
| Br— | H— | —(CH₂)₄— | CH₃CO— | p-F— |
| Br— | p-CH₃O— | —(CH₂)₂— | (CH₃CH₂)₂CHCO— | p-F— |
| Br— | p-F— | —(CH₂)₃— | CH₃CO— | p-F— |
| Br— | m-Cl— | —CH₂— | (CH₃)₃CCO— | o-CH₃— |
| Br— | m-CH₃O— | —(CH₂)₃— | CH₃(CH₂)₅CO— | o-F— |
| Br— | m-F— | —(CH₂)₃— | CH₃(CH₂)₆CO— | o-CH₃— |
| H— | p-CH₃O— | —(CH₂)₃— | CH₃CO— | p-F— |
| H— | p-F— | —(CH₂)₂— | CH₃(CH₂)₄CO— | p-CH₃— |
| H— | p-Cl— | —(CH₂)₃— | CH₃CO— | H— |
| H— | p-Cl— | —(CH₂)₃— | CH₃CH₂CO— | p-F— |
| H— | m-Cl— | —(CH₂)₄— | CH₃(CH₂)₃CO— | m-CH₃— |
| H— | m-CH₃O— | —(CH₂)₂— | CH₃CO— | m-Cl— |
| H— | m-CH₃O— | —(CH₂)₄— | (CH₃)₃CCO— | m-F— | and

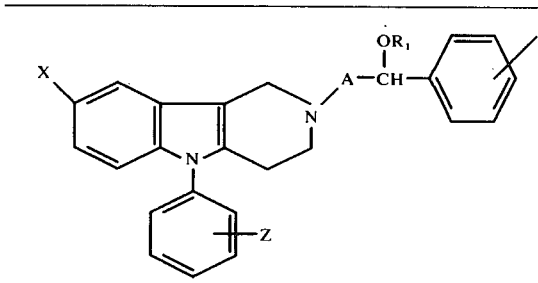

| X | Z | A | R₁ | Y |
|---|---|---|---|---|
| F— | p-F— | —(CH₂)₃— | CH₃CH₂CO— | p-F— |
| F— | p-F— | —(CH₂)₄— | CH₃CO— | p-CH₃— |
| F— | p-Cl— | —(CH₂)₃— | CH₃CO— | p-Cl— |
| F— | p-CH₃O— | —(CH₂)₅— | CH₃CO— | H— |
| F— | H— | —(CH₂)₃— | (CH₃CH₂)₂CHCO— | p-F— |
| F— | o-F— | —(CH₂)₃— | CH₃(CH₂)₅CO— | p-F— |
| F— | m-F— | —(CH₂)₄— | (CH₃)₃CCO— | m-F— |
| F— | m-Cl— | —CH₂— | CH₃(CH₂)₇CO— | m-F— |
| Cl— | p-F— | —CH₂— | CH₃CO— | p-Cl— |
| Cl— | p-F— | —(CH₂)₃— | CH₃(CH₂)CO— | p-CH₃— |
| Cl— | H— | —(CH₂)₅— | CH₃(CH₂)₃CO— | p-F— |
| Cl— | p-F— | —(CH₂)₃— | CH₃(CH₂)₇CO— | o-F— |
| Cl— | m-F— | —(CH₂)₂— | (CH₃)₃CCO— | o-Cl— |
| Cl— | o-CH₃O— | —(CH₂)₃— | CH₃CO— | m-Cl— |
| Cl— | m-F— | —(CH₂)₅— | CH₃(CH₂)₅CO— | m-CH₃— |
| Cl— | o-CH₃O— | —CH₂— | CH₃CH₂CO— | o-CH₃— |
| Br— | H— | —(CH₂)₃— | (CH₃CH₂)₂CHCO— | p-F— |
| Br— | p-CH₃O— | —(CH₂)₂— | CH₃CO— | p-F— |
| Br— | p-Cl— | —(CH₂)₂— | CH₃(CH₂)₄CO— | p-F— |
| Br— | m-Cl— | —CH₂— | CH₃CO— | o-CH₃— |
| Br— | m-F— | —(CH₂)₄— | CH₃(CH₂)₄CO— | m-F— |
| Br— | m-CH₃O— | —(CH₂)₃— | CH₃CH₂CO— | o-F— |
| Br— | m-Cl— | —(CH₂)₃— | (CH₃CH₂)₂CHCO— | o-F— |
| H— | p-CH₃O— | —(CH₂)₃— | CH₃CH₂CH(CH₃)CO— | p-F— |
| H— | p-CH₃O— | —(CH₂)₃— | CH₃CO— | p-Cl— |
| H— | p-F— | —(CH₂)₄— | (CH₃CH₂)₂CHCO— | H— |
| H— | p-Cl— | —(CH₂)₃— | CH₃(CH₂)₂CO— | p-F— |
| H— | p-Cl— | —(CH₂)₃— | CH₃CO— | p-F— |
| H— | p-F— | —(CH₂)₃— | (CH₃)₃CCO— | m-Cl— |
| H— | o-F— | —(CH₂)₃— | CH₃(CH₂)₄CO— | p-F— |
| H— | m-Cl— | —CH₂— | (CH₃CH₂)₂CHCO— | m-F— |
| H— | m-CH₃O— | —(CH₂)₂— | (CH₃)₂CHCO— | m-Cl— |
| H— | m-CH₃O— | —(CH₂)₄— | CH₃CH₂CO— | m-F— |

EXAMPLE 15

8-Fluoro-5-(p-fluorophenyl)-2-ethyl-1,2,3,4-tetrahydro-γ-carboline hydrochloride A. 8-fluoro-5-(p-fluorophenyl)-2-acetyl-1,2,3,4-tetrahydro-γ-carboline To a solution of 1.4 g. (4.9 m moles) of 8-fluoro-5-(p-fluorophenyl)-1,2,3,4-tetrahydro-γ-carboline in 10 ml. of methylene chloride cooled in an ice bath is added 1.49 g. (5.4 m moles) of triethyl amine and the solution allowed to stir for 5 min. To the stirred solution is added 423 mg. (5.4 m moles) of acetyl chloride dissolved in 5 ml. of methylene chloride, and the reaction mixture allowed to stir at room temperature for one hour. The mixture is decanted into 75 ml. of cold saturated sodium bicarbonate and subsequently extracted (3 × 50 ml.) with methylene chloride. The combined extracts are back-washed with a saturated brine solution and dried over magnesium sulfate. Removal of the solvent under reduced pressure provides the product as a glassy solid, which on trituration with hexane crystallizes to a white powder, 1.55 g., m.p. 150°-152° C.

Anal. Calc'd for $C_{19}H_{16}ON_2F_2$: C, 69.9; H, 4.9; N, 8.6. Found: C, 69.9; H, 5.3; N, 8.4.

B. 8-fluoro-5-(p-fluorophenyl)-2-ethyl-1,2,3,4-tetrahydro-γ-carboline hydrochloride A slurry of 243 mg. (6.4 m moles) of lithium aluminum hydride in 20 ml. of diethyl ether and 10 ml. of tetrahydrofuran cooled to 0°-5° C. is treated with 283 mg. (2.1 m moles) of aluminum chloride and the mixture allowed to stir in the cold for 30 min. While maintaining cooling, 871 mg. (2.6 m moles) of 8-fluoro-5-(p-fluorophenyl)-2-acetyl-1,2,3,4-tetrahydro-γ-carboline in 15 ml. of tetrahydrofuran is added dropwise over a 20 min. period to the metal hydride mixture. When the addition is complete, the reaction is allowed to stir for an additional 2 hrs., and then quenched in water. The ether is separated and the aqueous further extracted with the same solvent. The combined ether extracts are dried and concentrated to dryness to provide the crude base as a semi-crystalline oil, 868 mg.

The crude base (818 mg.), dissolved in diethyl ether, is converted to the hydrochloride salt using hydrogen chloride gas, 848 mg., m.p. 250°-253° C.

Anal. Calc'd for $C_{19}H_{13}N_2F_2 \cdot HCl \cdot \frac{1}{2} H_2O$: C, 63.8; H, 5.6; N, 7.8. Found: C, 63.7; H, 5.5; N, 8.1.

EXAMPLE 16

8-Fluoro-5-(p-fluorophenyl)-2-methyl-1,2,3,4-tetrahydro-γ-carboline hydrochloride To 316 mg. (8.3 m moles) of lithium aluminum hydride in 30 ml. of tetrahydrofuran is added dropwise 2.7 g. (7.58 m moles) of 8-fluoro-5-(p-fluorophenyl)-2-carbethoxy-1,2,3,4-tetrahydro-γ-carboline in 65 ml. of the same solvent, and the reaction mixture allowed to stir at room temperature for 2 hrs. Water (5 ml.) is added to quench the reaction and the mixture is filtered. The filtrate is concentrated in vacuo and the residual oil partitioned between benzene and water. The organic layer is separated, dried over magnesium sulfate and concentrated under reduced pressure to 2.6 g. of a yellow oil. The crude product is chromatographed on a silica gel column using methanol as the eluate, collected 5–10 ml. per fraction. Fractions 24 through 39 are combined and concentrated in vacuo to a yellow solid which on treatment with hydrogen chloride gas in diethyl ether yields the hydrochloride salt, 1.06 g., m.p. 295°–297° C.

Anal. Calc'd for $C_{18}H_{16}N_2F_2 \cdot HCl$: C, 64.6; H, 5.1; N, 8.4. Found: C, 64.3; H, 5.2; N, 8.4.

EXAMPLE 17

Employing the indicated procedure, and starting with the appropriate reagents, the following 2-alkyl-1,2,3,4-tetrahydro-γ-carboline hydrochlorides are synthesized:

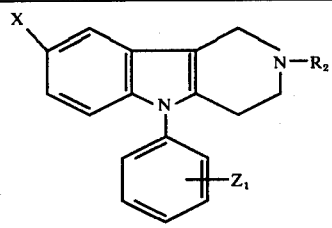

| X | $Z_1$ | $R_2$ | m.p., ° C. | Procedure |
|---|---|---|---|---|
| Cl— | H— | $CH_3$— | 281–283 | Example 16 |
| Br— | H— | $CH_3$— | 279–281 | Example 16 |
| F— | H— | $CH_3$— | 250–252 | Example 16 |
| H— | H— | $CH_3$— | 247–250 | Example 16 |
| $CH_3$— | H— | $CH_3$— | 128–130* | Example 16 |
| $CH_3O$— | H— | $CH_3$— | 265–266 | Example 16 |
| $CH_3O$— | p-F— | $CH_3$— | 262–265 | Example 16 |
| Cl— | p-F— | $CH_3$— | 286–288 | Example 16 |
| Cl— | H— | $C_2H_5$— | 272–274 | Example 15 |
| F— | p-F— | $n\text{-}C_3H_7$— | 276 dec. | Example 15 |
| F— | p-F— | $(CH_3)_3C(CH_2)_2$— | 274–276 | Example 15 |

*free base

EXAMPLE 18

Again the procedure of Example 15 or 16 is repeated, starting with appropriate amide or ester, to provide the following 2-alkyl-1,2,3,4-tetrahydro-γ-carbolines:

8-fluoro-5-(p-methoxyphenyl)-2-methyl-1,2,3,4-tetrahydro-γ-carboline (Example 16 procedure); 8-chloro-5-(p-methoxyphenyl)-2-methyl-1,2,3,4-tetrahydro-γ-carboline (Example 16 procedure); 8-methyl-5-(p-methoxyphenyl)-2-methyl-1,2,3,4-tetrahydro-γ-carboline (Example 16 procedure); 8-fluoro-5- 5-(p-chlorophenyl)-2-methyl-1,2,3,4-tetrahydro-γ-carboline (Example 16 procedure); 8-chloro-5-(p-chlorophenyl)-2-methyl-1,2,3,4-tetrahydro-γ-carboline (Example 16 procedure); 8-methyl-5-(p-chlorophenyl)-2-methyl-1,2,3,4-tetrahydro-γ-carboline (Example 16 procedure); 8-fluoro-5-(p-chlorophenyl)-2-n-butyl-1,2,3,4-tetrahydro-γ-carboline (Example 15 procedure); 8-fluoro-2-i-butyl-1,2,3,4-tetrahydro-γ-carboline (Example 15 procedure); 8-fluoro-5-(p-methoxyphenyl)-2-n-hexyl-1,2,3,4-tetrahydro-γ-carboline (Example 15 procedure); 8-fluoro-5-(p-chlorophenyl)-2-neo-pentyl-1,2,3,4-tetrahydro-γ-carboline (Example 15 procedure); 8-chloro-5-(p-fluorophenyl)-2-ethyl-1,2,3,4-tetrahydro-γ-carboline (Example 15 procedure); 8-methyl-5-phenyl-2-n-pentyl-1,2,3,4-tetrahydro-γ-carboline (Example 15 procedure); 5-p-methoxyphenyl-2-n-propyl-1,2,3,4-tetrahydro-γ-carboline (Example 15 procedure); 8-fluoro-5-(m-fluorophenyl)-2-methyl-1,2,3,4-tetrahydro-γ-carboline (Example 16 procedure); 8-fluoro-5-(o-fluorophenyl)-2-n-butyl-1,2,3,4-tetrahydro-γ-carboline (Example 15 procedure); 8-chloro-5-m-fluorophenyl)-2-hexyl-1,2,3,4-tetrahydro-γ-carboline (Example 15 procedure); 8-chloro-5-(o-chlorophenyl)-2-ethyl-1,2,3,4-tetrahydro-γ-carboline (Example 15 procedure); 8-bromo-5-(m-chlorophenyl)-2-neopentyl-1,2,3,4-tetrahydro-γ-carboline (Example 15 procedure); 8-bromo-5-(m-fluorophenyl)-2-n-pentyl-1,2,3,4-tetrahydro-γ-carboline (Example 15 procedure); 8-fluoro-5-(o-anisyl)-2-methyl-1,2,3,4-tetrahydro-γ-carboline (Example 16 procedure); 8-fluoro-5-(m-anisyl)-2-n-propyl-1,2,3,4-tetrahydro-γ-carboline (Example 15 procedure); 5-(o-fluorophenyl)-2-i-butyl-1,2,3,4-tetrahydro-γ-carboline (Example 15 procedure); 5-(m-chlorophenyl)-2-methyl-1,2,3,4-tetrahydro-γ-carboline (Example 16 procedure); 5-(m-anisyl)-2-ethyl-1,2,3,4-tetrahydro-γ-carboline (Example 15 procedure); 8-bromo-5-(m-anisyl)-2-n-hexyl-1,2,3,4-tetrahydro-γ-carboline (Example 15 procedure); 8-chloro-5-(o-anisyl)-2-n-pentyl-1,2,3,4-tetrahydro-γ-carboline (Example 15 procedure); 8-fluoro-5-(m-chlorophenyl)-2-n-hexyl-1,2,3,4-tetrahydro-γ-carboline (Example 15 procedure); and 8-fluoro-5-(o-chlorophenyl)-2-methyl-1,2,3,4-tetrahydro-γ-carboline (Example 16 procedure).

EXAMPLE 19

8-Chloro-5-phenyl-2-methyl-1,2,3,4-tetrahydro-γ-carboline hydrochloride

A. 8-chloro-2-methyl-1,2,3,4-tetrahydro-γ-carboline

To 35.6 g. (0.2 mole) of p-chlorophenylhydrazine hydrochloride is added with ice bath cooling 22.6 g. (0.2 mole) of 1-methyl-4-piperidone in 400 ml. of ethanol saturated with hydrogen chloride gas. When the addition is complete the ice bath is removed and the mixture heated to reflux for 2 hrs. and then allowed to cool overnight. Ethanol (100 ml.) is added and the precipitate allowed to stand for 3 hrs. at 5° C. The solids are filtered and dried at 50° C. at 25 m m pressure for several days, 11.0 g. The free base is liberated by treatment of the hydrochloride salt with 40% sodium hydroxide solution, the base being extracted with diethyl ether. Removal of the ether leaves the product as a tan solid, 7.3 g., m.p. 194°–196° C.

B. 8-chloro-5-phenyl-2-methyl-1,2,3,4-tetrahydro-γ-carboline hydrochloride

A mixture of 7.3 g. (33.2 m moles) of 8-chloro-2-methyl-1,2,3,4-tetrahydro-γ-carboline, 18.23 g. (0.116 mole) of bromobenzene, 10.4 g. (0.0364 mole) of cuprous bromide and 4.51 g. (0.0364 mole) of sodium carbonate in 125 ml. of N-methyl-2-pyrrolidinone is heated under a nitrogen atmosphere at an internal temperature of 184° for 9 hrs. The mixture is cooled, decanted into 300 ml. of water containing 30 ml. of ethylene diamine and sodium chloride and extracted with benzene. The combined extracts are back-washed with a saturated brine solution, dried over magnesium sulfate and concentrated in vacuo.

The crude product is chromatographed on a silia gel column using methanol as an eluate and fractions of 5 ml. each. Elution of the product is followed by thin layer chromatography, and the fractions containing the desired material are combined and concentrated under reduced pressure to dryness. The residual material is induced to crystallize by trituration with cold ethyl acetate, 945 mg., m.p. 124°–126° C.

The hydrochloride salt is prepared by treating a methanolic solution of the free base with hydrogen chloride gas to the saturation point, followed by the addition of an equal volume of diethyl ether, m.p. 281°–283° C.

Anal. Calc'd for $C_{18}H_{18}N_2Cl_2 \cdot HCl$: C, 64.9; H, 5.4; N, 8.4. Found: C, 64.6; H, 5.5; N, 8.4.

EXAMPLE 20

Starting with the appropriately substituted phenylhydrazine and requisite 1-alkyl-4-piperidone and halobenzene, and employing the procedure of Example 19, the following 5-aryl-2-alkyl-1,2,3,4-tetrahydro-γ-carbolines are synthesized:

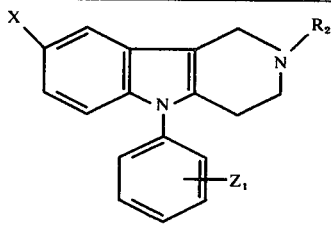

| X | $Z_1$ | $R_2$ |
|---|---|---|
| F— | p-F— | (CH₃)₂CH— |
| F— | p-F— | (CH₃)₃C— |
| F— | p-CH₃O— | (CH₃)₂CH— |
| F— | p-Cl— | CH₃CH₂CH(CH₃)— |
| F— | o-F— | (CH₃CH₂)₂CH— |
| F— | m-F— | (CH₃)₃C— |
| F— | m-CH₃O— | (CH₃)₂CH— |
| F— | o-Cl— | (CH₃)₂CH— |
| Cl— | p-F— | (CH₃CH₂)₂CH— |
| Cl— | p-F— | (CH₃)₂CH— |
| Cl— | m-F— | (CH₃)₃C— |
| Cl— | o-CH₃O— | CH₃CH₂CH(CH₃)— |
| Cl— | o-Cl— | (CH₃)₃C— |
| Br— | p-CH₃O— | (CH₃)₃C— |
| Br— | p-F— | (CH₃CH₂)₂CH— |
| Br— | m-Cl— | (CH₃)₂CH— |
| Br— | m-CH₃O— | (CH₃)₂CH— |
| Br— | m-CH₃O— | (CH₃)₃C— |
| H— | p-Cl— | (CH₃)₃C— |
| H— | p-F— | CH₃CH₂CH(CH₃)— |
| H— | o-F— | CH₃CH₂CH(CH₃)— |
| H— | m-CH₃O— | (CH₃)₂CH— |
| H— | m-Cl— | (CH₃)₃C— |

EXAMPLE 21

8-Fluoro-5-(p-fluorophenyl)-2-(3-benzoylpropyl)-1,2,3,4-tetrahydro-γ-carboline

A. 8-fluoro-5-(p-fluorophenyl)-2-(3-cyanopropyl)-1,2,3,4-tetrahydro-γ-carboline

A mixture of 25.0 g. (0.088 mole) of 8-fluoro-5-(p-fluorophenyl)-1,2,3,4-tetrahydro-γ-carboline, 18.3 g. (0.1232 mole) of bromobutyronitrile, 27.7 g. (0.264 mole) of sodium carbonate and 100 mg. of potassium iodide in 250 ml. of 4-methyl-2-pentanone is heated to the reflux temperature for 2 hrs. The reaction mixture is subsequently cooled and decanted into an equal volume of water. The organic solvent layer is separated, concentrated in vacuo, and the residual oil taken up in methylene chloride and washed successively with water and a saturated brine solution. The methylene chloride layer is dried over magnesium sulfate and concentrated under reduced pressure to 30 g. of a reddish oil. A small sample of the product in diethyl ether on treatment with hydrogen chloride gas provides the hydrochloride salt, m.p. 234°–236° C.

B. 8-fluoro-5-(p-fluorophenyl)-2-(3-benzoylpropyl)-1,2,3,4-tetrahydro-γ-carboline hydrochloride Phenyl magnesium bromide, prepared under standard Grignard reaction conditions from 4.8 ml. of bromobenzene and 1.1 g. of magnesium powder, in 80 ml. of diethyl ether is added dropwise to 4.0 g. (0.114 mole) of 8-fluoro-5-(p-fluorophenyl)-2-(3-cyanopropyl)-1,2,3,4-tetrahydro-γ-carboline over a period of 30 min. The reaction mixture is heated to reflux for 1 hour, and is then cooled and the ether decanted from the precipitate formed. The residue is washed several times with ether and is then added to 80 ml. of 12N hydrochloric acid in ice. The acid mixture is then heated to reflux for 1.5 hrs., cooled to room temperature and treated with sufficient 1.0N aqueous sodium hydroxide to make the solution basic. The product, which separates as an oil, is extracted into ether. Removal of the solvent provides 3.8 g. of the product as the free base. A small sample is converted to the hydrochloride salt, m.p. 208°–211° C.

Employing a similar sequence of reactions, and starting with the appropriate 5-aryl-2-cyanoalkyl-1,2,3,4-tetrahydro-α-carboline and Grignard reagent, the ketones of Examples 5, 6 and 7 are also prepared.

EXAMPLE 22

8-Fluoro-5-(p-fluorophenyl)-2-[4-(p-fluorophenyl)-3-butenyl]-1,2,3,4-tetrahydro-γ-carboline A solution of 2.0 g. (4.1 m moles) of 8-fluoro-5-(p-fluorophenyl)-2-[4-(p-fluorophenyl)-4-hydroxybutyl]-1,2,3,4-tetrahydro-γ-carboline in 20 ml. of ethanol and 50 ml. of 6N hydrochloric acid is heated to reflux for 4 hrs., and is then allowed to stir at room temperature for several days. The precipitated product is filtered and dried, 1.8 g. Further purification is effected by recrystallization from ethanol, m.p. 258°–259° C.

EXAMPLE 23

Starting with the carbinols of Examples 8, 9 and 10 and employing the procedure of Example 22, the following γ-carbolines are prepared:

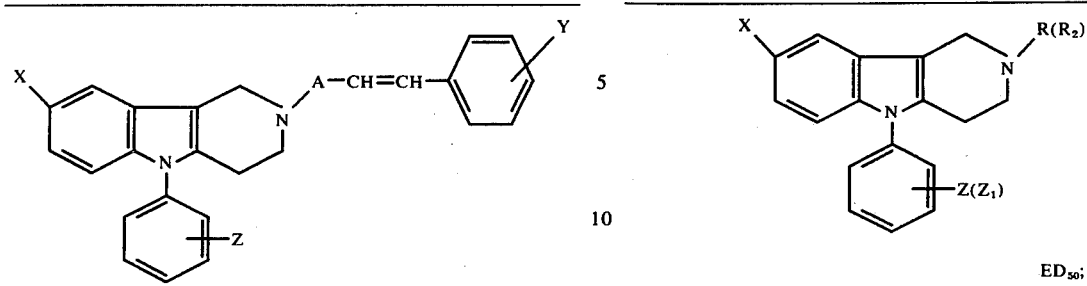

| X | Z | A | Y |
|---|---|---|---|
| F— | p-CH₃O— | —(CH₂)₂— | p-F— |
| Cl— | p-F— | —(CH₂)₂— | p-F— |
| F— | p-F— | —(CH₂)₂— | p-CH₃— |
| F— | p-F— | —(CH₂)₂— | p-Cl— |
| F— | p-F— | —CH₂— | p-F— |
| F— | p-F— | —(CH₂)₄— | p-F— |
| F— | o-F— | —(CH₂)₂— | p-F— |
| F— | m-F— | —(CH₂)₃— | m-F— |
| Cl— | p-Cl— | —CH₂— | p-F— |
| Cl— | p-CH₃O— | —CH₂— | p-Cl— |
| Cl— | m-F— | —CH₂— | o-Cl— |
| Cl— | o-CH₃O— | —(CH₂)₂— | m-Cl— |
| Cl— | m-F— | —(CH₂)₄— | m-CH₃— |
| Br— | H— | —CH₂— | p-F— |
| Br— | H— | —(CH₂)₂— | p-F— |
| Br— | m-CH₃O— | —(CH₂)₂— | o-F— |
| Br— | m-F— | —(CH₂)₂— | o-CH₃— |
| H— | p-CH₃O— | —CH₂— | p-F— |
| H— | p-CH₃O— | —CH₂— | p-Cl— |
| H— | p-F— | —(CH₂)₃— | H— |
| H— | p-Cl— | —(CH₂)₃— | H— |
| H— | m-Cl— | —(CH₂)₃— | m-CH₃— |
| H— | m-CH₃O— | —CH₂— | m-Cl— |
| H— | m-CH₃O— | —(CH₂)₃— | m-F— |

EXAMPLE 24

Test Procedures and Results

The effects of the compounds of the present invention on prominent amphetamine-induced symptoms were studied in rats by a rating scale modeled after the one reported by Quinton and Halliwell, and Weissman. Groups of five rats were placed in a covered plastic cage measuring approximately 26 cm. × 42 cm. × 16 cm. After a brief period of acclimation in the cage, the rats in each groups were treated intraperitoneally (i.p.) with the test compound. They were then treated 1, 5 and 24 hrs. later with d-amphetamine sulfate, 5 mg./kg. i.p. One hour after amphetamine was given each rat was observed for the characteristic amphetamine behavior of moving around the cage. On the basis of dose-response data after amphetamine it was possible to determine the effective dose of the compound necessary to antagonize or block the characteristic amphetamine behavior of cage movement for 50 percent of the rats tested ($ED_{50}$). The time of rating chosen coincides with the peak action of amphetamine which is 60–80 min. after treatment with this agent.

Employing the above-described procedure, the following compounds were tested for their ability to block the behavior effects of amphetamine, the results being reported as the $ED_{50}$ in mg./kg. at the indicated times:

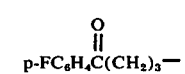

| X | Z (Z₁) | R (R₂) | 1 hr. | 5 hrs. | 24 hrs. |
|---|---|---|---|---|---|
| F— | F— | CH₃— | 1.0–3.2 | — | — |
| F— | H— | CH₃— | 3.2–10 | — | — |
| Cl— | F— | CH₃— | 1.0–3.2 | — | — |
| Br— | H— | CH₃— | 3.2–10 | — | — |
| Cl— | H— | CH₃— | 3.2–10 | — | — |
| F— | F— | C₂H₅— | 3.2–10 | >10 | >10 |
| F— | F— | n-C₃H₇— | 3.2–10 | >10 | >3.2 |
| F— | F— | (CH₃)₃C(CH₂)₂— | 1.0–3.2 | >10 | >10 |
| F— | F— | C₆H₅CH₂— | 3.2–10 | >10 | >10 |
| F— | F— | p-FC₆H₄CH=CH(CH₂)₂— | 3.2–10 | 1.0–3.2 | >3.2 |
| F— | F— | p-FC₆H₄C(O)(CH₂)₃— | 3.2–10 | >10 | — |
| Cl— | F— | p-FC₆H₄CH(OH)(CH₂)₃— | 0.1–0.32 | — | — |
| F— | F— | p-FC₆H₄CH(OH)(CH₂)₄— | 1.0–3.2 | 1.0–3.2 | >3.2 |
| H— | H— | CH₃— | 10–32 | | |
| H— | H— | CH₂C₆H₅— | >32 | | |
| Cl— | H— | C₂H₅— | 3.2–10 | | |
| Cl— | F— | p-CH₃C₆H₄CH(OH)(CH₂)₃— | .1–.32 | 1–3.2 | |
| F— | OCH₃— | p-FC₆H₄C(O)(CH₂)₃— | >10 | | |
| F— | OCH₃— | p-FC₆H₄CH(OH)(CH₂)₃— | 1–3.2 | | |
| F— | F— | p-CH₃C₆H₄C(O)(CH₂)₃— | 3.2–10 | >10 | |
| F— | F— | p-FC₆H₄—C(CH₃)(OH)—(CH₂)₃— | 1–3.2 | 1–3.2 | >3.2 |
| F— | F— | p-FC₆H₄CH(OH)—(CH₂)₂— | 3.2–10 | >10 | |
| chlorpromazine | | | 7 | | |
| F— | F— | C₆H₅C(O)—(CH₂)₃— | >10 | | |

EXAMPLE 25

8-Chloro-5-(p-fluorophenyl)-2-[4-(p-fluorophenyl)-4-hydroxybutyl]-1,2,3,4-tetrahydro-γ-carboline acetate Five grams of 8-chloro-5-(p-fluorophenyl)-2-[4-(p-fluorophenyl)-4-hydroxybutyl]-1,2,3,4-tetrahydro-γ-carboline hydrochloride in 75 ml. of water is treated with 3 ml. of water containing 1.0 g. of sodium hydroxide, and the liberated free base extracted into 150 ml. of diethyl ether. The ether layer is separated, dried over magnesium sulfate and treated with 1 ml. of glacial acetic acid. The organic solvent and excess acetic acid are removed under reduced pressure and the residue triturated with hexane and filtered.

In a similar manner, other acid addition salts, especially those which are pharmaceutically acceptable, can be prepared.

EXAMPLE 26

Tablets

A tablet base is prepared by blending the following ingredients in the proportion by weight indicated:

| | |
|---|---|
| Sucrose, U.S.P. | 80.3 |
| Tapioca starch | 13.2 |
| Magnesium stearate | 6.5 |

Into this tablet base there is blended sufficient 8-fluoro-5-(p-fluorophenyl)-2-[4-(p-fluorophenyl)-4-hydroxybutyl]-1,2,3,4-tetrahydro-γ-carboline hydrochloride to provide tablets containing 1.0, 2.5, 5.0 and 10 mg. of active ingredient per tablet. The compositions are each compressed into tablets, each weighing 360 mg., by conventional means.

EXAMPLE 27

Capsules

A blend is prepared containing the following ingredients:

| | |
|---|---|
| Calcium carbonate, U.S.P. | 17.6 |
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 |

To this blend is added sufficient 8-chloro-5-(p-fluorophenyl)-2-[4-(p-fluorophenyl)-4-hydroxybutyl]-1,2,3,4-tetrahydro-γ-carboline hydrochloride to provide capsules containing 1.0, 2.5, 5.0 and 10 mg. of active ingredient per capsule. The compositions are filled into conventional hard gelatin capsules in the amount of 350 mg. per capsule.

EXAMPLE 28

Suspension

A suspension of 8-fluoro-5-(p-fluorophenyl)-2-[4-(p-tolyl)-4-hydroxybutyl]-1,2,3,4-tetrahydro-γ-carboline sulfate is prepared with the following composition:

| | |
|---|---|
| Effective ingredient | g. 25.00 |
| 70% aqueous sorbital | g. 741.29 |
| Glycerine, U.S.P. | g. 185.35 |
| Gum acacia (10% solution) | ml. 100.00 |
| Polyvinylpyrrolidone | g. 0.50 |
| Distilled water, sufficient to make 1 liter | |

To this suspension, various sweeteners and flavorants are added to improve the palatability of the suspension. The suspension contains approximately 25 mg. of effective agent per milliliter.

EXAMPLE 29

Sesame oil is sterilized by heating to 120° C. for 2 hrs. To this oil, a sufficient quantity of pulverized 8-fluoro-5-(p-fluorophenyl)-2-[4-(p-fluorophenyl)-4-hydroxybutyl]-1,2,3,4-tetrahydro-γ-carboline hydrochloride to make a 0.025% suspension by weight. The solid is thoroughly dispersed in the oil by use of a colloid mill, It is then filtered through a 100–250 mesh screen and poured into sterile vials and sealed.

What is claimed is:

1. A compound selected from those of the formula

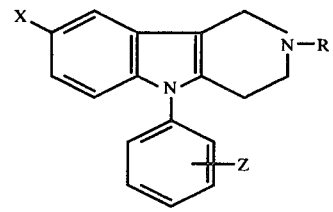

and the pharmaceutically acceptable acid addition salts thereof, wherein

X is selected from the group consisting of fluoro, chloro, bromo and hydrogen;

Z is selected from the group consisting of hydrogen, fluoro, chloro and methoxy and R is of the formula

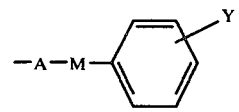

wherein A is alkylene having 1 to 5 carbon atoms,

M is selected from the group consisting of

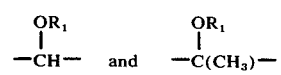

wherein $R_1$ is hydrogen and Y is selected from the group consisting of fluoro, chloro, methyl and hydrogen.

2. The compound of claim 1 wherein X is fluoro, Z is p-fluoro, A is —(CH$_2$)$_3$—, M is

and Y is p-fluoro.

3. The compound of claim 1 wherein X is fluoro, Z is p-fluoro, A is —(CH$_2$)$_3$—, M is

and Y is hydrogen.

4. The compound of claim 1 wherein X is fluoro, Z is p-fluoro, A is —(CH₂)₃—, M is

and Y is p-chloro.

5. The compound of claim 1 wherein X is fluoro, Z is p-fluoro, A is —(CH₂)₃—, M is

and Y is p-methyl.

6. The compound of claim 1 wherein X is fluoro, Z is p-fluoro, A is —(CH₂)₂—, M is

and Y is p-fluoro.

7. The compound of claim 1 wherein X is fluoro, Z is p-fluoro, A is —(CH₂)₄—, M is

and Y is p-fluoro.

8. The compound of claim 1 wherein X is fluoro, Z is m-fluoro, A is —(CH₂)₃—, M is

and Y is p-fluoro.

9. The compound of claim 1 wherein X is fluoro, Z is o-fluoro, A is —(CH₂)₃—, M is

and Y is p-fluoro.

10. The compound of claim 1 wherein X is chloro, Z is fluoro, A is —(Ch₂)₃—, M is

and Y is p-fluoro.

11. The compound of claim 1 wherein Y is brome, Z is p-fluoro, A is —(CH₂)₃—, M is

and Y is p-fluoro.

12. The compound of claim 1 wherein X is fluoro, Z is p-fluoro, A is —(CH₂)₃—, M is

and Y is m-fluoro.

13. The compound of claim 1 wherein X is fluoro, Z is p-methoxy, A is —(CH₂)₃—, M is

and Y is p-fluoro.

14. The compound of claim 1 wherein X is fluoro, Z is p-methoxy, A is —(CH₂)₃—, M is

and Y is p-methyl.

15. The compound of claim 1 wherein X is fluoro, Z is p-methoxy, A is —(Ch₂)₃—, M is

and Y is p-chloro.

16. The compound of claim 1 wherein X is fluoro, Z is hydrogen, A is —(CH₂)₃—, M is

and Y is p-fluoro.

17. The compound of claim 1 wherein X is chloro, Z is hydrogen, A is —(CH₂)₃—, M is

and Y is p-fluoro.

18. The compound of claim 1 wherein X is fluoro, Z is hydrogen, A is —(CH₂)₃—, M is

and Y is p-methyl.

19. The compound of claim 1 wherein X is chloro, Z is hydrogen, A is —(CH₂)₃—, M is

and Y is p-methyl.

20. The compound of claim 1 wherein X is fluoro, Z is p-chloro, A is —(CH$_2$)$_3$—, M is

and Y is p-fluoro.

21. The compound of claim 1 wherein X is fluoro, Z is p-chloro, A is —(CH$_2$)$_3$—, M is

and Y is p-chloro.

22. The compound of claim 1 wherein X is fluoro, Z is p-chloro, A is —(CH$_2$)$_3$—, M is

−CH(OH)− and Y is hydrogen.

23. The compound of claim 1 wherein X is fluoro, Z is p-fluoro, A is —(CH$_2$)$_3$—, M is

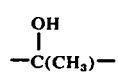

and Y is p-fluoro.

24. The compound of claim 1 wherein X is chloro, Z is p-fluoro, A is —(CH$_2$)$_3$—, M is

−C(CH$_3$)(OH)− and Y is p-fluoro.

25. The compound of claim 1 wherein X is fluoro, Z is hydrogen, A is —(CH$_2$)$_3$—, M is

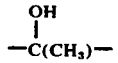

and Y is p-fluoro.

* * * * *

UNITED STATES PATENT AND TRADEMARK OFFICE
CERTIFICATE OF CORRECTION

PATENT NO. : 4,001,263
DATED : January 4, 1977
INVENTOR(S) : Jacob J. Plattner et al.

It is certified that error appears in the above-identified patent and that said Letters Patent are hereby corrected as shown below:

Col. 11, line 66, after "carboline" insert -- 8-bromo-5-(p-fluorophenyl)-2-[3-(p-fluorobenzoyl)propyl]-1,2,3,4-tetrahydro-γ-carboline, --.
Col. 12, line 16, "8-5-" should read -- 8-chloro-5- --.
Col. 12, line 24, "toul" should read -- tolyl --.
Col. 12, line 32, "8-5" should read -- 8-fluoro-5- --.
Col. 12, line 40, "fluoro-5-" should read -- chloro-5- --.
Col. 12, line 49, "8-5" should read -- 8-fluoro-5- --.
Col. 12, line 51, "8-5" should read -- 8-fluoro-5- --.
Col. 12, line 61, "[-fluoro-" should read -- 8-fluoro- --.
Col. 17, line 22, "65.6" should read -- 65.5 --.
Col. 26, line 5, "8-fluoro-2-i-butyl-1,2,3,4-tetrahydro- -carboline" should read -- 8-fluoro-5-(p-fluorophenyl)-2-i-butyl-1,2,3,4-tetrahydro-γ-carboline --.

Col. 33, line 67, "Y" should read -- X --.
Col. 33, line 67, "brome" should read -- bromo --.

Signed and Sealed this thirtieth Day of August 1977

[SEAL]

Attest:

RUTH C. MASON
Attesting Officer

C. MARSHALL DANN
Commissioner of Patents and Trademarks